US008323312B2

(12) United States Patent  
Clark

(10) Patent No.: US 8,323,312 B2
(45) Date of Patent: Dec. 4, 2012

(54) CLOSURE DEVICE

(75) Inventor: Ian J. Clark, West Bloomfield, MI (US)

(73) Assignee: Abbott Laboratories, Abbott Park, IL (US)

( * ) Notice: Subject to any disclaimer, the term of this patent is extended or adjusted under 35 U.S.C. 154(b) by 124 days.

(21) Appl. No.: 12/481,377

(22) Filed: Jun. 9, 2009

(65) Prior Publication Data

US 2010/0160958 A1   Jun. 24, 2010

Related U.S. Application Data

(60) Provisional application No. 61/139,995, filed on Dec. 22, 2008.

(51) Int. Cl.
A61B 17/122 (2006.01)
(52) U.S. Cl. ...................................................... 606/216
(58) Field of Classification Search .................. 606/138, 606/139, 151, 153, 155, 157, 158, 213, 214, 606/215, 216, 217, 142, 221; 623/23.72
See application file for complete search history.

(56) References Cited

U.S. PATENT DOCUMENTS

| 287,046 | A | 10/1883 | Norton |
| 438,400 | A | 10/1890 | Brennen |
| 1,088,393 | A | 2/1914 | Backus |
| 1,331,401 | A | 2/1920 | Summers |
| 1,596,004 | A | 8/1926 | De Bengoa |
| 1,647,958 | A | 11/1927 | Ciarlante |
| 1,880,569 | A | 10/1932 | Weis |
| 2,087,074 | A | 7/1937 | Tucker |
| 2,254,620 | A | 9/1941 | Miller |
| 2,316,297 | A | 4/1943 | Southerland et al. |
| 2,371,978 | A | 3/1945 | Perham |
| 2,453,227 | A | 11/1948 | James |
| 2,583,625 | A | 1/1952 | Bergan |
| 2,684,070 | A | 7/1954 | Kelsey |
| 2,910,067 | A | 10/1959 | White |

(Continued)

FOREIGN PATENT DOCUMENTS

AU  2003297432  7/2004

(Continued)

OTHER PUBLICATIONS

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42-No. 3, Institution Department of Plastic and Reconstructive Surgery, Albert Einstein College of Medicine and Montefiore Medical Center, Bronx, NY.

(Continued)

Primary Examiner — Ryan Severson
Assistant Examiner — Rachel S Papeika
(74) Attorney, Agent, or Firm — Workman Nydegger; Randy Shen

(57) ABSTRACT

Devices and methods are disclosed herein for a closure device. A closure device includes a body movable from a pre-deployed configuration towards a deployed configuration, a plurality of tissue-engaging portions extending from the body. At least two of the tissue-engaging portions are separated by a first distance in the deployed configuration and a second distance in the pre-deployed configuration in which the first distance is smaller than the second distance. The closure device also includes a plurality of device-capture features secured to the body. The device-capture features are configured to move the tissue-engaging portions to a separation greater than the first distance.

23 Claims, 18 Drawing Sheets

U.S. PATENT DOCUMENTS

| | | |
|---|---|---|
| 2,944,311 A | 7/1960 | Schneckenberger |
| 2,951,482 A | 9/1960 | Sullivan |
| 2,969,887 A | 1/1961 | Darmstadt et al. |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,482,428 A | 12/1969 | Kapitanov et al. |
| 3,494,533 A | 2/1970 | Green et al. |
| 3,510,923 A | 5/1970 | Blake |
| 3,523,351 A | 8/1970 | Filia |
| 3,586,002 A | 6/1971 | Wood et al. |
| 3,604,425 A | 9/1971 | Le Roy |
| 3,618,447 A | 11/1971 | Goins |
| 3,677,243 A | 7/1972 | Nerz |
| 3,757,629 A | 9/1973 | Schneider |
| 3,805,337 A | 4/1974 | Branstetter |
| 3,823,719 A | 7/1974 | Cummings |
| 3,828,791 A | 8/1974 | Santos |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A | 6/1976 | Murray |
| 3,985,138 A | 10/1976 | Jarvik |
| 4,007,743 A | 2/1977 | Blake |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,273,129 A | 6/1981 | Boebel |
| 4,274,415 A | 6/1981 | Kanamoto et al. |
| 4,278,091 A | 7/1981 | Borzone |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,396,139 A | 8/1983 | Hall et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Valaincourt |
| 4,526,174 A | 7/1985 | Froehlich |
| 4,586,503 A | 5/1986 | Kirsch et al. |
| 4,592,498 A | 6/1986 | Braun et al. |
| 4,595,559 A | 6/1986 | Fleischhacker |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,651,737 A | 3/1987 | Deniega |
| 4,664,305 A | 5/1987 | Blake, III et al. |
| 4,665,906 A | 5/1987 | Jervis |
| 4,687,469 A | 8/1987 | Osypka |
| 4,693,249 A | 9/1987 | Schenck et al. |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A | 10/1992 | Nakao et al. |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,209,756 A | 5/1993 | Seedhorm et al. |
| 5,217,024 A | 6/1993 | Dorsey et al. |
| 5,222,974 A | 6/1993 | Kensey et al. |
| 5,226,908 A | 7/1993 | Yoon |

| Patent Number | Date | Inventor(s) |
|---|---|---|
| 5,236,435 A * | 8/1993 | Sewell, Jr. .................... 606/138 |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Janota |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,309,927 A | 5/1994 | Welch |
| 5,318,542 A | 6/1994 | Hirsch et al. |
| 5,320,639 A | 6/1994 | Rudnick |
| 5,327,908 A | 7/1994 | Gerry |
| 5,330,445 A | 7/1994 | Haaga |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| RE34,866 E | 2/1995 | Kensey et al. |
| 5,392,978 A | 2/1995 | Velez et al. |
| 5,395,030 A | 3/1995 | Kuramoto et al. |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,561 A | 10/1995 | Voda |
| 5,464,413 A | 11/1995 | Siska, Jr. et al. |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,486,195 A | 1/1996 | Myers et al. |
| 5,497,933 A | 3/1996 | DeFonzo et al. |
| 5,507,744 A | 4/1996 | Tay et al. |
| 5,507,755 A | 4/1996 | Gresl et al. |
| 5,522,840 A | 6/1996 | Krajicek |
| 5,527,322 A | 6/1996 | Klein et al. |
| 5,536,251 A | 7/1996 | Evard et al. |
| 5,540,712 A | 7/1996 | Kleshinski et al. |
| 5,540,716 A | 7/1996 | Hlavacek |
| 5,544,802 A | 8/1996 | Crainich |
| 5,547,474 A | 8/1996 | Kloeckl et al. |
| 5,560,532 A | 10/1996 | DeFonzo et al. |
| 5,571,120 A | 11/1996 | Yoon |
| 5,573,784 A | 11/1996 | Badylak et al. |
| 5,575,771 A | 11/1996 | Walinsky |
| 5,584,879 A | 12/1996 | Reimold et al. |
| 5,591,205 A | 1/1997 | Fowler |
| 5,593,412 A | 1/1997 | Martinez et al. |
| 5,601,602 A | 2/1997 | Fowler |
| 5,609,597 A | 3/1997 | Lehrer |
| 5,613,974 A | 3/1997 | Andreas et al. |
| 5,618,291 A | 4/1997 | Thompson et al. |
| 5,620,452 A | 4/1997 | Yoon |
| 5,620,461 A | 4/1997 | Muijs et al. |
| 5,634,936 A | 6/1997 | Lindon et al. |
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,649,959 A | 7/1997 | Hannam et al. |
| D383,539 S | 9/1997 | Croley |
| 5,674,231 A | 10/1997 | Green et al. |
| 5,676,689 A | 10/1997 | Kensey et al. |
| 5,676,974 A | 10/1997 | Valdes et al. |
| 5,681,280 A | 10/1997 | Rusk et al. |
| 5,681,334 A | 10/1997 | Evans et al. |
| 5,683,405 A | 11/1997 | Yacoubian et al. |
| 5,690,674 A | 11/1997 | Diaz |
| 5,695,504 A | 12/1997 | Gifford, III et al. |
| 5,695,505 A | 12/1997 | Yoon |
| 5,695,524 A | 12/1997 | Kelley et al. |
| 5,700,273 A | 12/1997 | Buelna et al. |
| 5,713,899 A | 2/1998 | Marnay et al. |
| 5,715,987 A | 2/1998 | Kelley et al. |
| 5,716,375 A | 2/1998 | Fowler |
| 5,720,755 A | 2/1998 | Dakov |
| 5,725,498 A | 3/1998 | Janzen et al. |
| 5,725,552 A | 3/1998 | Kotula et al. |
| 5,725,554 A | 3/1998 | Simon et al. |
| 5,728,110 A | 3/1998 | Vidal et al. |
| 5,728,114 A | 3/1998 | Evans et al. |
| 5,728,122 A | 3/1998 | Leschinsky et al. |
| 5,728,132 A | 3/1998 | Van Tassel et al. |
| 5,728,133 A | 3/1998 | Kontos |
| 5,732,872 A | 3/1998 | Bolduc et al. |
| 5,735,873 A | 4/1998 | MacLean |
| 5,749,826 A | 5/1998 | Faulkner |
| 5,752,966 A | 5/1998 | Chang |
| 5,755,726 A | 5/1998 | Pratt et al. |
| 5,755,778 A | 5/1998 | Kleshinski |
| 5,766,217 A | 6/1998 | Christy |
| 5,766,246 A | 6/1998 | Mulhauser et al. |
| 5,769,870 A | 6/1998 | Salahieh et al. |
| 5,776,147 A | 7/1998 | Dolendo |
| 5,779,707 A | 7/1998 | Bertholet et al. |
| 5,782,844 A | 7/1998 | Yoon et al. |
| 5,782,860 A | 7/1998 | Epstein et al. |
| 5,782,861 A | 7/1998 | Cragg et al. |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich et al. |
| 5,810,851 A | 9/1998 | Yoon |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |

| | | | | | | |
|---|---|---|---|---|---|---|
| 5,833,698 | A | 11/1998 | Hinchliffe et al. | 6,113,612 | A | 9/2000 | Swanson et al. |
| 5,843,167 | A | 12/1998 | Dwyer et al. | 6,117,125 | A | 9/2000 | Rothbarth et al. |
| 5,853,421 | A | 12/1998 | Leschinsky et al. | 6,117,148 | A | 9/2000 | Ravo |
| 5,853,422 | A | 12/1998 | Huebsch et al. | 6,117,157 | A | 9/2000 | Tekulve |
| 5,855,312 | A | 1/1999 | Toledano | 6,117,159 | A | 9/2000 | Huebsch et al. |
| 5,858,082 | A | 1/1999 | Cruz et al. | 6,120,524 | A | 9/2000 | Taheri |
| 5,860,991 | A | 1/1999 | Klein et al. | 6,126,675 | A | 10/2000 | Schervinsky et al. |
| 5,861,005 | A | 1/1999 | Kontos | 6,136,010 | A | 10/2000 | Modesitt et al. |
| 5,868,755 | A | 2/1999 | Kanner et al. | 6,146,385 | A | 11/2000 | Torrie et al. |
| 5,868,762 | A | 2/1999 | Cragg et al. | 6,149,660 | A | 11/2000 | Laufer et al. |
| 5,868,763 | A | 2/1999 | Spence et al. | 6,149,667 | A | 11/2000 | Hovland et al. |
| 5,871,474 | A | 2/1999 | Hermann et al. | 6,152,144 | A | 11/2000 | Lesh et al. |
| 5,871,501 | A | 2/1999 | Leschinsky et al. | 6,152,936 | A | 11/2000 | Christy et al. |
| 5,871,525 | A | 2/1999 | Edwards et al. | 6,152,937 | A | 11/2000 | Peterson et al. |
| 5,873,876 | A | 2/1999 | Christy | 6,165,204 | A | 12/2000 | Levinson et al. |
| 5,879,366 | A | 3/1999 | Shaw et al. | 6,171,277 | B1 | 1/2001 | Ponzi |
| 5,891,088 | A | 4/1999 | Thompson et al. | 6,171,329 | B1 | 1/2001 | Shaw et al. |
| 5,897,487 | A | 4/1999 | Ouchi | 6,174,322 | B1 | 1/2001 | Schneidt |
| 5,902,310 | A | 5/1999 | Foerster et al. | 6,179,849 | B1 | 1/2001 | Yencho et al. |
| 5,904,697 | A | 5/1999 | Gifford, III et al. | 6,179,860 | B1 | 1/2001 | Fulton, III et al. |
| 5,906,631 | A | 5/1999 | Imran | 6,193,708 | B1 | 2/2001 | Ken et al. |
| 5,907,893 | A | 6/1999 | Zadno-Azizi et al. | 6,193,734 | B1 | 2/2001 | Bolduc et al. |
| 5,910,155 | A | 6/1999 | Ratcliff et al. | 6,197,042 | B1 | 3/2001 | Ginn et al. |
| 5,919,207 | A | 7/1999 | Taheri | 6,198,974 | B1 | 3/2001 | Webster, Jr. |
| 5,922,009 | A | 7/1999 | Epstein et al. | 6,200,329 | B1 | 3/2001 | Fung et al. |
| 5,928,231 | A | 7/1999 | Klein et al. | 6,206,895 | B1 | 3/2001 | Levinson |
| 5,928,251 | A | 7/1999 | Aranyi et al. | 6,206,913 | B1 | 3/2001 | Yencho et al. |
| 5,935,147 | A | 8/1999 | Kensey et al. | 6,206,931 | B1 | 3/2001 | Cook et al. |
| 5,938,667 | A | 8/1999 | Peyser et al. | 6,210,407 | B1 | 4/2001 | Webster |
| 5,941,890 | A | 8/1999 | Voegele et al. | 6,220,248 | B1 | 4/2001 | Voegele et al. |
| 5,947,999 | A | 9/1999 | Groiso | 6,221,102 | B1 | 4/2001 | Baker et al. |
| 5,951,518 | A | 9/1999 | Licata et al. | 6,231,561 | B1 | 5/2001 | Frazier et al. |
| 5,951,575 | A | 9/1999 | Bolduc et al. | 6,245,079 | B1 | 6/2001 | Nobles et al. |
| 5,951,576 | A | 9/1999 | Wakabayashi | 6,248,124 | B1 | 6/2001 | Pedros et al. |
| 5,951,589 | A | 9/1999 | Epstein et al. | 6,254,617 | B1 | 7/2001 | Spence et al. |
| 5,957,900 | A | 9/1999 | Ouchi | 6,254,642 | B1 | 7/2001 | Taylor |
| 5,957,936 | A | 9/1999 | Yoon et al. | 6,258,115 | B1 | 7/2001 | Dubrul |
| 5,957,938 | A | 9/1999 | Zhu et al. | 6,267,773 | B1 | 7/2001 | Gadberry et al. |
| 5,957,940 | A | 9/1999 | Tanner et al. | 6,273,903 | B1 | 8/2001 | Wilk |
| 5,964,782 | A | 10/1999 | Lafontaine et al. | 6,276,704 | B1 | 8/2001 | Suiter |
| 5,976,161 | A | 11/1999 | Kirsch et al. | 6,277,140 | B2 | 8/2001 | Ginn et al. |
| 5,984,934 | A | 11/1999 | Ashby et al. | 6,280,460 | B1 | 8/2001 | Bolduc et al. |
| 5,984,948 | A | 11/1999 | Hasson | 6,287,322 | B1 | 9/2001 | Zhu et al. |
| 5,984,949 | A | 11/1999 | Levin | 6,296,657 | B1 | 10/2001 | Brucker |
| 5,993,468 | A | 11/1999 | Rygaard | 6,302,898 | B1 | 10/2001 | Edwards et al. |
| 5,993,476 | A | 11/1999 | Groiso | 6,305,891 | B1 | 10/2001 | Burlingame |
| 6,001,110 | A | 12/1999 | Adams | 6,319,258 | B1 | 11/2001 | McAllen, III et al. |
| 6,004,341 | A | 12/1999 | Zhu et al. | 6,322,580 | B1 | 11/2001 | Kanner |
| 6,007,563 | A | 12/1999 | Nash et al. | 6,328,727 | B1 | 12/2001 | Frazier et al. |
| 6,010,517 | A | 1/2000 | Baccaro | 6,329,386 | B1 | 12/2001 | Mollison |
| 6,013,084 | A | 1/2000 | Ken et al. | 6,334,865 | B1 | 1/2002 | Redmond et al. |
| 6,015,815 | A | 1/2000 | Mollison | 6,348,064 | B1 | 2/2002 | Kanner |
| 6,019,779 | A | 2/2000 | Thorud et al. | 6,355,052 | B1 | 3/2002 | Neuss et al. |
| 6,022,372 | A | 2/2000 | Kontos | 6,358,258 | B1 | 3/2002 | Arcia et al. |
| 6,024,750 | A | 2/2000 | Mastri | 6,375,671 | B1 | 4/2002 | Kobayashi et al. |
| 6,024,756 | A | 2/2000 | Huebsch et al. | D457,958 | S | 5/2002 | Dycus |
| 6,030,364 | A | 2/2000 | Durgin et al. | 6,383,208 | B1 | 5/2002 | Sancoff et al. |
| 6,030,413 | A | 2/2000 | Lazarus | 6,391,048 | B1 | 5/2002 | Ginn et al. |
| 6,033,427 | A | 3/2000 | Lee | 6,395,015 | B1 | 5/2002 | Borst et al. |
| 6,036,703 | A | 3/2000 | Evans et al. | 6,398,752 | B1 | 6/2002 | Sweezer et al. |
| 6,036,720 | A | 3/2000 | Abrams et al. | 6,402,765 | B1 | 6/2002 | Monassevitch et al. |
| 6,045,570 | A | 4/2000 | Epstein et al. | 6,409,739 | B1 | 6/2002 | Nobles et al. |
| 6,048,358 | A | 4/2000 | Barak | 6,419,669 | B1 | 7/2002 | Frazier et al. |
| 6,056,768 | A | 5/2000 | Cates et al. | 6,423,054 | B1 | 7/2002 | Ouchi |
| 6,056,769 | A | 5/2000 | Epstein et al. | 6,425,911 | B1 | 7/2002 | Akerfeldt et al. |
| 6,056,770 | A | 5/2000 | Epstein et al. | 6,428,472 | B1 | 8/2002 | Haas |
| 6,059,800 | A | 5/2000 | Hart et al. | 6,428,548 | B1 | 8/2002 | Durgin et al. |
| 6,059,825 | A | 5/2000 | Hobbs et al. | 6,443,158 | B1 | 9/2002 | Lafontaine et al. |
| 6,063,085 | A | 5/2000 | Tay et al. | 6,443,963 | B1 | 9/2002 | Baldwin et al. |
| 6,063,114 | A | 5/2000 | Nash et al. | 6,447,540 | B1 | 9/2002 | Fontaine et al. |
| 6,071,300 | A | 6/2000 | Brenneman et al. | 6,450,391 | B1 | 9/2002 | Kayan et al. |
| 6,077,281 | A | 6/2000 | Das | 6,458,130 | B1 | 10/2002 | Frazier et al. |
| 6,077,291 | A | 6/2000 | Das | 6,461,364 | B1 | 10/2002 | Ginn et al. |
| 6,080,182 | A | 6/2000 | Shaw et al. | 6,482,224 | B1 | 11/2002 | Michler et al. |
| 6,080,183 | A | 6/2000 | Tsugita et al. | 6,488,692 | B1 | 12/2002 | Spence et al. |
| 6,083,242 | A | 7/2000 | Cook | 6,500,115 | B2 | 12/2002 | Krattiger et al. |
| 6,090,130 | A | 7/2000 | Nash et al. | 6,506,210 | B1 | 1/2003 | Kanner |
| 6,102,271 | A | 8/2000 | Longo et al. | 6,508,828 | B1 | 1/2003 | Akerfeldt et al. |
| 6,110,184 | A | 8/2000 | Weadock | 6,517,569 | B2 | 2/2003 | Mikus et al. |

| Patent No. | Date | Inventor |
|---|---|---|
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,551,319 B2 | 4/2003 | Lieberman |
| 6,569,173 B1 | 5/2003 | Blatter et al. |
| 6,569,185 B2 | 5/2003 | Ungs |
| 6,572,629 B2 | 6/2003 | Kalloo et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,599,303 B1 | 7/2003 | Peterson et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,616,686 B2 | 9/2003 | Coleman et al. |
| 6,623,509 B2 | 9/2003 | Ginn |
| 6,623,510 B2 | 9/2003 | Carley et al. |
| 6,626,918 B1 | 9/2003 | Ginn et al. |
| 6,626,920 B2 | 9/2003 | Whayne |
| 6,632,197 B2 | 10/2003 | Lyon |
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,645,255 B2 | 11/2003 | Atkinson |
| 6,652,538 B2 | 11/2003 | Kayan et al. |
| 6,652,556 B1 | 11/2003 | VanTassel et al. |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,685,707 B2 | 2/2004 | Roman et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,743,195 B2 | 6/2004 | Zucker |
| 6,743,243 B1 | 6/2004 | Roy et al. |
| 6,743,259 B2 | 6/2004 | Ginn |
| 6,749,621 B2 | 6/2004 | Pantages et al. |
| 6,749,622 B2 | 6/2004 | McGuckin et al. |
| 6,755,842 B2 | 6/2004 | Kanner et al. |
| 6,767,356 B2 | 7/2004 | Kanner et al. |
| 6,776,785 B1 | 8/2004 | Yencho et al. |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,906 B2 | 1/2005 | Ginn |
| 6,846,319 B2 | 1/2005 | Ginn et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,397 B2 | 11/2005 | Ginn |
| 6,989,003 B2 | 1/2006 | Wing et al. |
| 6,989,016 B2 | 1/2006 | Tallarida et al. |
| 7,001,398 B2 * | 2/2006 | Carley et al. .......... 606/142 |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,108,709 B2 | 9/2006 | Cummins |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,261,716 B2 | 8/2007 | Strobel et al. |
| 7,311,720 B2 | 12/2007 | Mueller et al. |
| 7,316,704 B2 | 1/2008 | Bagaoisan et al. |
| 7,322,995 B2 | 1/2008 | Buckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walburg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,727 B2 | 10/2008 | Cole et al. |
| 7,431,729 B2 | 10/2008 | Chanduszko |
| 7,465,286 B2 | 12/2008 | Patterson et al. |
| 7,533,790 B1 | 5/2009 | Knodel et al. |
| 7,582,103 B2 | 9/2009 | Young et al. |
| 7,582,104 B2 | 9/2009 | Corcoran et al. |
| 7,597,706 B2 | 10/2009 | Kanner et al. |
| D611,144 S | 3/2010 | Reynolds |
| 7,780,696 B2 | 8/2010 | Daniel et al. |
| 7,806,904 B2 | 10/2010 | Carley et al. |
| 7,819,895 B2 | 10/2010 | Ginn et al. |
| 7,841,502 B2 | 11/2010 | Walberg et al. |
| 7,842,068 B2 | 11/2010 | Ginn |
| 7,850,709 B2 | 12/2010 | Cummins et al. |
| 7,850,797 B2 | 12/2010 | Carley et al. |
| 7,854,810 B2 | 12/2010 | Carley et al. |
| 7,857,828 B2 | 12/2010 | Jabba et al. |
| 7,931,671 B2 | 4/2011 | Tenerz |
| 7,967,842 B2 | 6/2011 | Bakos |
| 8,103,327 B2 | 1/2012 | Harlev et al. |
| 8,105,352 B2 | 1/2012 | Egnelöv |
| 2001/0007077 A1 | 7/2001 | Ginn et al. |
| 2001/0031972 A1 | 10/2001 | Robertson et al. |
| 2001/0046518 A1 | 11/2001 | Sawhney |
| 2001/0047180 A1 | 11/2001 | Grudem et al. |
| 2002/0026215 A1 | 2/2002 | Redmond et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0058960 A1 | 5/2002 | Hudson et al. |
| 2002/0077657 A1 | 6/2002 | Ginn et al. |
| 2002/0082641 A1 | 6/2002 | Ginn et al. |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0183786 A1 | 12/2002 | Girton |
| 2002/0183787 A1 | 12/2002 | Wahr et al. |
| 2002/0198562 A1 | 12/2002 | Ackerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0023248 A1 | 1/2003 | Parodi |
| 2003/0032981 A1 | 2/2003 | Kanner et al. |
| 2003/0045893 A1 | 3/2003 | Ginn |
| 2003/0055455 A1 | 3/2003 | Yang et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093096 A1 | 5/2003 | McGuckin et al. |
| 2003/0097140 A1 | 5/2003 | Kanner |

| | | |
|---|---|---|
| 2003/0109890 A1 | 6/2003 | Kanner et al. |
| 2003/0125766 A1 | 7/2003 | Ding |
| 2003/0144695 A1 | 7/2003 | McGuckin, Jr. et al. |
| 2003/0158577 A1 | 8/2003 | Pantages et al. |
| 2003/0158578 A1 | 8/2003 | Pantages et al. |
| 2003/0195504 A1 | 10/2003 | Tallarida et al. |
| 2003/0195561 A1 | 10/2003 | Carley et al. |
| 2004/0009205 A1 | 1/2004 | Sawhney |
| 2004/0009289 A1 | 1/2004 | Carley et al. |
| 2004/0049224 A1 | 3/2004 | Buehlmann et al. |
| 2004/0059376 A1* | 3/2004 | Breuniger .................. 606/216 |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0127940 A1 | 7/2004 | Ginn et al. |
| 2004/0143290 A1 | 7/2004 | Brightbill |
| 2004/0153122 A1 | 8/2004 | Palermo |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0149117 A1 | 7/2005 | Khosravi et al. |
| 2005/0152949 A1 | 7/2005 | Hotchkiss et al. |
| 2005/0165357 A1 | 7/2005 | McGuckin et al. |
| 2005/0169974 A1 | 8/2005 | Tenerez et al. |
| 2005/0177189 A1 | 8/2005 | Ginn et al. |
| 2005/0187564 A1 | 8/2005 | Jayaraman |
| 2005/0216057 A1 | 9/2005 | Coleman et al. |
| 2005/0222614 A1 | 10/2005 | Ginn et al. |
| 2005/0245876 A1 | 11/2005 | Khosravi et al. |
| 2005/0267528 A1 | 12/2005 | Ginn et al. |
| 2005/0267530 A1 | 12/2005 | Cummins |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0064115 A1 | 3/2006 | Allen et al. |
| 2006/0100664 A1 | 5/2006 | Pai et al. |
| 2006/0167484 A1* | 7/2006 | Carley et al. .................. 606/151 |
| 2006/0190014 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206146 A1 | 9/2006 | Tenerz |
| 2006/0253037 A1 | 11/2006 | Ginn et al. |
| 2006/0253072 A1 | 11/2006 | Pai et al. |
| 2006/0287674 A1 | 12/2006 | Ginn et al. |
| 2006/0293698 A1 | 12/2006 | Douk |
| 2007/0005093 A1 | 1/2007 | Cox |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0049968 A1 | 3/2007 | Sibbitt, Jr. et al. |
| 2007/0060950 A1 | 3/2007 | Khosravi et al. |
| 2007/0083230 A1 | 4/2007 | Javois |
| 2007/0112304 A1 | 5/2007 | Voss |
| 2007/0112365 A1 | 5/2007 | Hilal et al. |
| 2007/0123816 A1 | 5/2007 | Zhu et al. |
| 2007/0123817 A1 | 5/2007 | Khosravi et al. |
| 2007/0172430 A1 | 7/2007 | Brito et al. |
| 2007/0179527 A1 | 8/2007 | Eskuri et al. |
| 2007/0203507 A1 | 8/2007 | McLaughlin et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0275036 A1 | 11/2007 | Green, III et al. |
| 2007/0276416 A1 | 11/2007 | Ginn et al. |
| 2007/0276488 A1 | 11/2007 | Wachter et al. |
| 2007/0282352 A1 | 12/2007 | Carley et al. |
| 2007/0282373 A1 | 12/2007 | Ashby et al. |
| 2008/0004636 A1 | 1/2008 | Walberg et al. |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0093414 A1 | 4/2008 | Bender et al. |
| 2008/0114395 A1 | 5/2008 | Mathisen et al. |
| 2008/0177288 A1 | 7/2008 | Carlson |
| 2008/0210737 A1 | 9/2008 | Ginn et al. |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0300628 A1 | 12/2008 | Ellingwood |
| 2008/0312666 A1 | 12/2008 | Ellingwood et al. |
| 2008/0312686 A1 | 12/2008 | Ellingwood |
| 2008/0312740 A1 | 12/2008 | Wachter et al. |
| 2008/0319475 A1 | 12/2008 | Clark |
| 2009/0054912 A1 | 2/2009 | Heanue et al. |
| 2009/0112306 A1 | 4/2009 | Bonsignore et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0171388 A1 | 7/2009 | Dave et al. |
| 2009/0177212 A1 | 7/2009 | Carley et al. |
| 2009/0187215 A1 | 7/2009 | Mackiewicz et al. |
| 2009/0216267 A1 | 8/2009 | Willard et al. |
| 2009/0227938 A1 | 9/2009 | Fasching et al. |
| 2009/0230168 A1 | 9/2009 | Coleman et al. |
| 2009/0254119 A1 | 10/2009 | Sibbitt, Jr. et al. |
| 2009/0287244 A1 | 11/2009 | Kokish |
| 2009/0312789 A1 | 12/2009 | Kassab et al. |
| 2010/0114156 A1 | 5/2010 | Mehl |
| 2010/0114159 A1 | 5/2010 | Roorda et al. |
| 2010/0168790 A1 | 7/2010 | Clark |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0217132 A1 | 8/2010 | Ellingwood et al. |
| 2011/0178548 A1 | 7/2011 | Tenerz |
| 2012/0035630 A1 | 2/2012 | Roorda |

FOREIGN PATENT DOCUMENTS

| | | |
|---|---|---|
| CA | 2 339 060 | 2/2000 |
| DE | 197 11 288 | 10/1998 |

| | | |
|---|---|---|
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |
| JP | 2000102546 | 4/2000 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

Tomoaki Hinohara, Percutaneous vascular surgery (Prostar® Plus and Techstar® for femoral artery site closure), Interventional Cardiology Newsletter, May-Jul. 1997, pp. 19-28, vol. 5-No. 3-4.

UT Aker et al, Immediate arterial hemostasis after cardiac catheterization: initial experience with a new puncture closure device, Cathet Cardiovasc Diagn, Mar. 1994, pp. 228-232, vol. 33-No. 3, Missouri Baptist Medical Center, St. Louis.

Wei Qu et al, an absorbable pinned-ring device for microvascular anastomosis of vein grafts: Experimental studies, Microsurgery 1999, Mar. 1999, pp. 128-134, vol. 19-No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25-No. 7.

U.S. Appl. No. 09/478,179, Nov. 6, 2000, Notice of Allowance.
U.S. Appl. No. 09/546,998, May 6, 2002, Notice of Allowance.
U.S. Appl. No. 09/610,238, Mar. 26, 2001, Notice of Allowance.

U.S. Appl. No. 09/610,238, Sep. 5, 2001, Office Action.
U.S. Appl. No. 09/610,238, Feb. 11, 2002, Notice of Allowance.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Advisory Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,835, Sep. 11, 2003, Office Action.
U.S. Appl. No. 12/897,358, filed Oct. 4, 2010, Carley.
U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/945,646, filed Nov. 12, 2010, Carley et al.
U.S. Appl. No. 12/966,923, filed Dec. 13, 2010, Cummins et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 10/435,104, Jan. 12, 2011, Issue Notification.
U.S. Appl. No. 10/638,115, Dec. 22, 2010, Issue Notification.
U.S. Appl. No. 11/048,503, Dec. 8, 2010, Issue Notification.
U.S. Appl. No. 11/113,549, Jan. 4, 2011, Office Action.
U.S. Appl. No. 12/113,851, Dec. 16, 2010, Office Action.
U.S. Appl. No. 12/114,091, Dec. 17, 2010, Office Action.
U.S. Appl. No. 12/402,398, Jan. 24, 2011, Office Action.
U.S. Appl. No. 12/945,646, Jan. 20, 2011, Office Action.
U.S. Appl. No. 13/017,636, filed Jan. 31, 2011, Carley et al.
U.S. Appl. No. 10/616,832, Jan. 26, 2011, Issue Notification.
U.S. Appl. No. 11/152,562, Jan. 26, 2011, Issue Notification.
U.S. Appl. No. 13/026,989, filed Feb. 14, 2011, Cummins.
U.S. Appl. No. 10/264,306, Feb. 16, 2011, Issue Notification.
U.S. Appl. No. 11/767,818, Feb. 16, 2011, Office Action.
U.S. Appl. No. 13/030,922, filed Feb. 18, 2011, Cummins.
U.S. Appl. No. 10/356,214, Feb. 23, 2011, Issue Notification.
U.S. Appl. No. 13/039,087, filed Mar. 2, 2011, Palermo et al.
U.S. Appl. No. 11/852,190, Mar. 2, 2011, Office Action.
U.S. Appl. No. 12/122,603, Mar. 3, 2011, Office Action.
U.S. Appl. No. 11/958,281, Mar. 10, 2011, Office Action.
U.S. Appl. No. 11/532,576, Mar. 16, 2011, Issue Notification.
U.S. Appl. No. 11/396,731, Mar. 22, 2011, Office Action.
U.S. Appl. No. 11/427,297, Mar. 21, 2011, Office Action.
U.S. Appl. No. 10/147,774, Apr. 6, 2011, Issue Notification.
U.S. Appl. No. 10/682,459, Apr. 1, 2011, Notice of Allowance.
U.S. Appl. No. 12/403,277, Mar. 31, 2011, Office Action.
U.S. Appl. No. 12/122,603, Apr. 22, 2011, Office Action.
U.S. Appl. No. 12/113,851, Apr. 27, 2011, Office Action.
U.S. Appl. No. 13/112,618, filed May 20, 2011, Gianotti et al.
U.S. Appl. No. 13/112,631, filed May 20, 2011, Voss.
U.S. Appl. No. 12/114,031, May 11, 2011, Office Action.
U.S. Appl. No. 12/143,020, May 11, 2011, Office Action.
U.S. Appl. No. 12/955,859, May 26, 2011, Office Action.
U.S. Appl. No. 13/153,594, filed Jun. 6, 2011, Reyes et al.
U.S. Appl. No. 10/667,144, Jun. 6, 2011, Office Action.
U.S. Appl. No. 60/693,531, filed Jun. 24, 2005, Carly.
U.S. Appl. No. 60/696,069, filed Jul. 1, 2005, Pantages et al.
U.S. Appl. No. 60/711,279, filed Aug. 24, 2005, Sibbitt, Jr. et al.
U.S. Appl. No. 60/726,985, filed Oct. 14, 2005, Sibbitt, Jr. et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/097,072, filed Sep. 15, 2008, Sibbitt, Jr. et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.
U.S. Appl. No. 09/866,551, filed May 25, 2001, Ginn.
U.S. Appl. No. 12/113,092, filed Apr. 30, 2008, Ginn et al.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 12/961,331, filed Dec. 6, 2010, Voss.
"Hand tool for forming telephone connections—comprises pliers with reciprocably driven ram crimping clip around conductors against anvil", Derwent-ACC-No. 1978-B8090A.
Database WPI; Section PQ, Week 200120; Derwent Publications Ltd., London GB; Class P31, AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62-No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77-No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6-No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72-No. 5, Department of Cardiology, Academic Hospital Maastricht, The Netherlands.
Harrith M. Hasson M.D., Laparoscopic Cannula Cone with Means for Cannula Stabilization and Wound Closure, The Journal of the American Association of Gynecologic Laparoscopists, May 1998, pp. 183-185, vol. 5-No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42-No. 3, Division of Neurosurgery, University of Alberta, Edmonton, Canada.
Jeremy L Gilbert PhD, Wound Closure Biomaterials and Devices, Shock., Mar. 1999, p. 226, vol. 11-No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27-No. 6, Department of Surgery, Mercy Hospital of Pittsburgh, PA.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6-No. 5, Orlando Regional Medical Center, FL.
Michael Gianturco, A Play on Catheterization, Forbes, Dec. 1996, p. 146, vol. 158-No. 15.
OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183-No. 4.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63-No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.

Peter Rhee MD et al, Use of Titanium Vascular Staples in Trauma, Journal of Trauma-Injury Infection & Critical Care, Dec. 1998, pp. 1097-1099, vol. 45-No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.

SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19-No. 6, Gen Hosp North, Dept Dianost & Intervent Radiol, Nurnberg, Germany (Reprint).

Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, vol. 83-No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.-No. 2, Supplement 1.

Stretch Comb by Scunci, retrieved via internet at www.scunci.com/productdetail by examiner on Oct. 9, 2007, publication date unavailable.

Swee Lian Tan, MD, PhD, FACS, Explanation of Infected Hemostatic Puncture Closure Devices—A Case Report, Vascular and Endovascular Surgery, 1999, pp. 507-510, vol. 33-No. 5, Parkland Medical Center, Derry, New Hampshire.

Sy Nakada et al, Comparison of newer laparoscopic port closure techniques in the porcine model, J Endourol, Oct. 1995, pp. 397-401, vol. 9-No. 5, Department of Surgery/Urology, University of Wisconsin Medical School, Madison.

Taber's Cyclopedic Medical Dictionary, 18th Ed. 1997, pp. 747 and 1420.

U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,813, Jun. 4, 2001, Notice of Allowance.
U.S. Appl. No. 09/933,299, Feb. 26, 2003, Office Action.
U.S. Appl. No. 09/933,299, Jun. 16, 2003, Notice of Allowance.
U.S. Appl. No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.
U.S. Appl. No. 10/081,717, Sep. 29, 2003, Notice of Allowance.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Notice of Allowance.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/147,774, Jun. 8, 2010, Office Action.
U.S. Appl. No. 10/147,774, Dec. 2, 2010, Notice of Allowance.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Amendment Under 312.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/264,306, Oct. 29, 2010, Notice of Allowance.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/356,214, Sep. 3, 2010, Notice of Allowance.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Examiner's Amendment.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/435,104, Oct. 5, 2010, Notice of Allowance.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Mar. 24, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/517,004, Nov. 23, 2010, Issue Notification.
U.S. Appl. No. 10/519,778, Feb. 23, 2006, Office Action.

U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, Aug. 17, 2010, Notice of Allowance.
U.S. Appl. No. 10/541,083, Dec. 1, 2010, Issue Notification.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/616,832, Sep. 20, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/638,115, Aug. 13, 2010, Notice of Allowance.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/667,144, Jun. 22, 2010, Office Action.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/682,459, Oct. 12, 2010, Office Action.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/787,073, Sep. 15, 2010, Issue Notification.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/152,562, Sep. 16, 2010, Notice of Allowance.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No. 11/198,811, Oct. 20, 2010, Issue Notification.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/390,586, Jun. 24, 2009, Office Action.
U.S. Appl. No. 11/390,586, Jul. 6, 2010, Office Action.
U.S. Appl. No. 11/396,141, May 22, 2009, Office Action.
U.S. Appl. No. 11/396,141, Aug. 26, 2009, Office Action.
U.S. Appl. No. 11/396,141, May 4, 2010, Office Action.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/406,203, Oct. 6, 2010, Issue Notification.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/427,297, Jan. 30, 2009, Office Action.
U.S. Appl. No. 11/427,297, Sep. 15, 2009, Office Action.
U.S. Appl. No. 11/427,297, Sep. 15, 2010, Office Action.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/427,309, Nov. 15, 2010, Office Action.
U.S. Appl. No. 11/455,993, Feb. 17, 2009, Office Action.
U.S. Appl. No. 11/455,993, Dec. 16, 2009, Office Action.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,576, Mar. 1, 2010, Office Action.
U.S. Appl. No. 11/532,576, Apr. 23, 2010, Office Action.
U.S. Appl. No. 11/532,576, Oct. 13, 2010, Notice of Allowance.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/675,462, Dec. 10, 2009, Office Action.
U.S. Appl. No. 11/675,462, Aug. 31, 2010, Office Action.
U.S. Appl. No. 11/744,089, Nov. 26, 2008, Office Action.
U.S. Appl. No. 11/744,089, Aug. 14, 2009, Office Action.
U.S. Appl. No. 11/757,108, Nov. 25, 2009, Office Action.

U.S. Appl. No. 11/767,818, Dec. 24, 2009, Office Action.
U.S. Appl. No. 11/767,818, Mar. 22, 2010, Office Action.
U.S. Appl. No. 11/767,818, Sep. 30, 2010, Office Action.
U.S. Appl. No. 11/852,190, Jun. 24, 2010, Office Action.
U.S. Appl. No. 11/852,190, Nov. 1, 2010, Office Action.
U.S. Appl. No. 11/958,281, Sep. 2, 2010, Office Action.
U.S. Appl. No. 11/958,281, Oct. 8, 2010, Office Action.
U.S. Appl. No. 11/958,295, Aug. 27, 2009, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 11/959,334, Jul. 23, 2010, Notice of Allowance.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,928, Oct. 25, 2010, Office Action.
U.S. Appl. No. 12/106,937, Mar. 30, 2009, Office Action.
U.S. Appl. No. 12/106,937, Nov. 18, 2009, Office Action.
U.S. Appl. No. 12/113,851, Apr. 27, 2010, Office Action.
U.S. Appl. No. 12/113,851, Jun. 24, 2010, Office Action.
U.S. Appl. No. 12/114,031, Oct. 5, 2010, Office Action.
U.S. Appl. No. 12/114,031, Nov. 22, 2010, Office Action.
U.S. Appl. No. 12/402,398, Mar. 9, 2010, Office Action.
U.S. Appl. No. 12/402,398, May 20, 2010, Office Action.
U.S. Appl. No. 12/403,256, Dec. 16, 2009, Office Action.
U.S. Appl. No. 12/403,256, Mar. 30, 2010, Office Action.
U.S. Appl. No. 12/403,256, Aug. 19, 2010, Notice of Allowance.
U.S. Appl. No. 12/403,256, Nov. 23, 2010, Issue Notification.
U.S. Appl. No. 12/403,277, Jul. 8, 2010, Office Action.
U.S. Appl. No. 12/403,277, Oct. 12, 2010, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 29/296,370, Feb. 10, 2010, Issue Notification.
U.S. Appl. No. 12/114,091, Oct. 27, 2010, Office Action.
U.S. Appl. No. 11/959,334, Nov. 10, 2010, Issue Notification.
U.S. Appl. No. 10/667,144, Oct. 28, 2011, Notice of Allowance.
U.S. Appl. No. 12/945,646, Oct. 26, 2011, Office Action.
U.S. Appl. No. 12/122,603, Sep. 23, 2011, Office Action.
U.S. Appl. No. 12/393,877, Sep. 29, 2011, Office Action.
U.S. Appl. No. 13/222,899, filed Aug. 31, 2011, Carley et al.
U.S. Appl. No. 11/396,731, Sep. 1, 2011, Office Action.
U.S. Appl. No. 12/143,020, Aug. 31, 2011, Office Action.
U.S. Appl. No. 12/897,358, Aug. 22, 2011, Office Action.
U.S. Appl. No. 13/026,989, Sep. 16, 2011, Office Action.
U.S. Appl. No. 11/675,462, Aug. 3, 2011, Office Action.
U.S. Appl. No. 12/114,031, Aug. 2, 2011, Office Action.
U.S. Appl. No. 12/114,091, Jul. 7, 2011, Office Action.
U.S. Appl. No. 12/135,858, Jul. 13, 2011, Office Action.
U.S. Appl. No. 12/945,646, Jul. 6, 2011, Office Action.
U.S. Appl. No. 12/955,859, Jul. 21, 2011, Office Action.
U.S. Appl. No. 12/393,877, Dec. 13, 2011, Office Action.
U.S. Appl. No. 12/941,809, Dec. 13, 2011, Restriction Requirement.
U.S. Appl. No. 12/955,859, Dec. 15, 2011, Office Action.
U.S. Appl. No. 11/767,818, Feb. 3, 2012, Notice of Allowance.
U.S. Appl. No. 12/114,031, Mar. 6, 2012, Office Action.
U.S. Appl. No. 12/135,858, Feb. 16, 2012, Office Action.
U.S. Appl. No. 12/143,020, Feb. 23, 2012, Notice of Allowance.
U.S. Appl. No. 12/338,977, Jan. 19, 2012, Office Action.
U.S. Appl. No. 12/548,274, Dec. 28, 2011, Office Action.
U.S. Appl. No. 12/548,274, Mar. 2, 2012, Office Action.
U.S. Appl. No. 12/608,769, Feb. 10, 2012, Office Action.
U.S. Appl. No. 12/642,319, Feb. 27, 2012, Office Action.
U.S. Appl. No. 12/684,400, Feb. 13, 2012, Office Action.
U.S. Appl. No. 12/684,470, Mar. 23, 2012, Office Action.
U.S. Appl. No. 12/684,542, Jan. 30, 2012, Office Action.
U.S. Appl. No. 12/684,562, Dec. 28, 2011, Office Action.
U.S. Appl. No. 12/684,562, Feb. 16, 2012, Office Action.
U.S. Appl. No. 12/684,569, Jan. 27, 2012, Office Action.
U.S. Appl. No. 13/308,227, filed Nov. 30, 2011, Yibarren.
U.S. Appl. No. 11/390,586, May 3, 2012, Notice of Allowance.
U.S. Appl. No. 12/113,851, Mar. 29, 2012, Office Action.
U.S. Appl. No. 12/114,091, Apr. 5, 2012, Office Action.
U.S. Appl. No. 12/393,877, May 21, 2012, Office Action.
U.S. Appl. No. 12/403,277, Apr. 3, 2012, Office Action.
U.S. Appl. No. 12/684,400, May 9, 2012, Office Action.
U.S. Appl. No. 12/684,542, Apr. 16, 2012, Office Action.
U.S. Appl. No. 12/688,065, Apr. 26, 2012, Office Action.
U.S. Appl. No. 12/897,358, May 2, 2012, Issue Notification.
U.S. Appl. No. 12/966,923, May 16, 2012, Issue Notification.
U.S. Appl. No. 12/608,773, Jun. 7, 2012, Office Action.
U.S. Appl. No. 13/026,989, Jun. 8, 2012, Office Action.
U.S. Appl. No. 13/525,839, filed Jun. 18, 2012, Carley et al.
U.S. Appl. No. 11/427,297, Jun. 26, 2012, Notice of Allowance.
U.S. Appl. No. 11/767,818, Jul. 4, 2012, Issue Notification.
U.S. Appl. No. 12/338,977, Jul. 11, 2012, Office Action.
U.S. Appl. No. 12/688,065, Mar. 13, 2012, Office Action.
U.S. Appl. No. 12/724,304, Feb. 10, 2012, Office Action.
U.S. Appl. No. 12/897,358, Jan. 12, 2012, Notice of Allowance.
U.S. Appl. No. 12/897,358, Mar. 5, 2012, Notice of Allowance.
U.S. Appl. No. 12/941,809, Jan. 30, 2012, Office Action.
U.S. Appl. No. 12/945,646, Feb. 21, 2012, Notice of Allowance.
U.S. Appl. No. 12/966,923, Feb. 3, 2012, Notice of Allowance.
U.S. Appl. No. 12/973,204, Mar. 7, 2012, Notice of Allowance.
U.S. Appl. No. 12/987,792, Mar. 13, 2012, Office Action.
U.S. Appl. No. 12/143,020, May 30, 2012, Issue Notification.
U.S. Appl. No. 12/941,809, Jun. 1, 2012, Office Action.
U.S. Appl. No. 12/945,646, May 30, 2012, Issue Notification.
U.S. Appl. No. 12/973,204, May 30, 2012, Issue Notification.
U.S. Appl. No. 11/390,586, Jul. 18, 2012, Issue Notification.
U.S. Appl. No. 12/608,773, Jul. 20, 2012, Office Action.
U.S. Appl. No. 12/684,569, Jul. 30, 2012, Office Action.
U.S. Appl. No. 13/039,087, Jul. 17, 2012, Office Action.
U.S. Appl. No. 11/675,462, Dec. 22, 2011, Notice of Allowance.
U.S. Appl. No. 12/684,470, Dec. 20, 2011, Restriction Requirement.
U.S. Appl. No. 12/684,569, Dec. 20, 2011, Restriction Requirement.
U.S. Appl. No. 11/675,462, mailed Aug. 15, 2012, Issue Notification.
U.S. Appl. No. 11/744,089, mailed Aug. 8, 2012, Office Action.
U.S. Appl. No. 12/850,242, mailed Aug. 6, 2012, Office Action.
U.S. Appl. No. 12/955,859, mailed Aug. 6, 2012, Office Action.
U.S. Appl. No. 12/608,769, mailed Aug. 22, 2012, Office Action.
U.S. Appl. No. 12/642,319, mailed Aug. 28, 2012, Office Action.
U.S. Appl. No. 12/848,642, mailed Sep. 20, 2012, Office Action.
U.S. Appl. No. 12/987,792, mailed Sep. 17, 2012, Office Action.

* cited by examiner

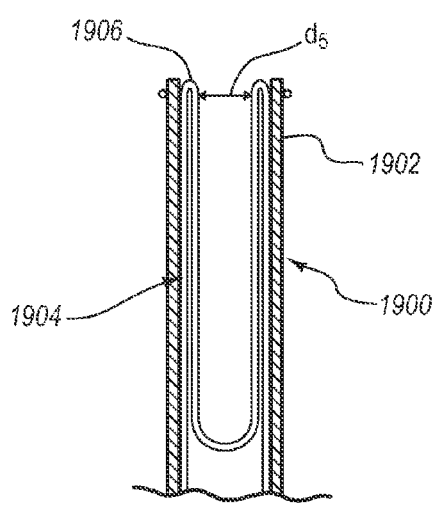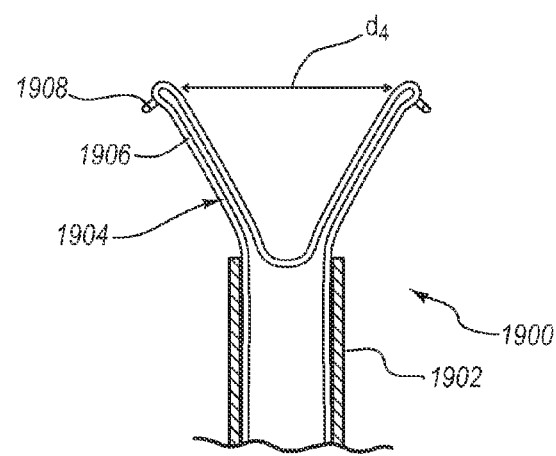
Fig. 19E
Fig. 19F

CLOSURE DEVICE

CROSS-REFERENCE TO RELATED APPLICATIONS

This U.S. patent application claims the benefit of and priority to U.S. Provisional Patent Application having Ser. No. 61/139,995, filed on Dec. 22, 2008, the disclosure of which is incorporated herein by reference in its entirety.

FIELD OF THE INVENTION

The present invention relates generally to medical devices, and more particular to device, apparatus, and methods for managing access through tissue.

BACKGROUND OF THE INVENTION

Catheterization and interventional procedures, such as angioplasty or stenting, generally are performed by inserting a hollow needle through a patient's skin and tissue into the vascular system. A guide wire may be advanced through the needle and into the patient's blood vessel accessed by the needle. The needle is then removed, enabling an introducer sheath to be advanced over the guide wire into the vessel, e.g., in conjunction with or subsequent to a dilator.

A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

In practice, the introducer sheath is generally inserted into the patient's vasculature using the modified Seldinger technique. In the Seldinger technique, a needle is first inserted into the vessel and a guidewire then follows through the needle. Next, the needle is removed and a sheath/dilator combination is advanced over the guidewire. The dilator expands the puncture in the vessel to a size suitable to receive the distal end of an introducer sheath. After the distal end of the sheath is disposed within the vessel, the dilator and guidewire are removed, thereby allowing access to the vessel lumen or other body lumen via the inserted introducer sheath.

Upon completing the procedure, the devices and introducer sheath would be removed, leaving a puncture site, i.e. an arteriotomy in the vessel wall. Traditionally, external pressure would be applied to the puncture site until clotting and wound sealing occur; however, the patient must remain bedridden for a substantial period after clotting to ensure closure of the wound. This procedure, however, may be time consuming and expensive, requiring as much as an hour of a physician's or nurse's time. It is also uncomfortable for the patient and requires that the patient remain immobilized in the operating room, catheter lab, or holding area. In addition, a risk of hematoma exists from bleeding before hemostasis occurs. Risks of additional complications can also include pseudo aneurism, retro-peritoneal hematoma, and/or A-V fistula.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. Another technique has been suggested that involves percutaneously suturing the puncture site, such as that disclosed in U.S. Pat. No. 5,304,204, issued to Hathaway et al. Such apparatuses were designed for permanent deployment, without regard for subsequent removal.

BRIEF SUMMARY

Devices and methods are disclosed herein for a closure device. A closure device includes a body movable from a pre-deployed configuration towards a deployed configuration, a plurality of tissue-engaging portions extending from the body. Two or more of the tissue-engaging portions are separated by a first distance in the deployed configuration and a second distance in the pre-deployed configuration. The first distance can be smaller than the second distance. The closure device also includes a plurality of device-capture features secured to or forming part of the body. The device-capture features can be engaged to move the tissue-engaging portions to a separation greater than the first distance.

It is to be understood that both the foregoing general description and the following detailed description are exemplary and are intended to provide further explanation of the invention claimed. The accompanying figures, which are incorporated in and constitute part of this specification, are included to illustrate and provide a further understanding of the method and system of the invention. Together with the description, the figures serve to explain the principles of the invention.

BRIEF DESCRIPTION OF THE DRAWINGS

In order to describe the manner in which the above-recited and other advantages and features of the invention can be obtained, a more particular description of the invention briefly described above will be rendered by reference to specific examples thereof that are illustrated in the appended drawings. Understanding that these drawings depict only typical examples of the invention and are not therefore to be considered to be limiting of its scope, the invention will be described and explained with additional specificity and detail through use of the accompanying drawings.

FIGS. 19C-19H illustrate the closure device being moved from a deployed state to an expanded state.

Figure 1A:
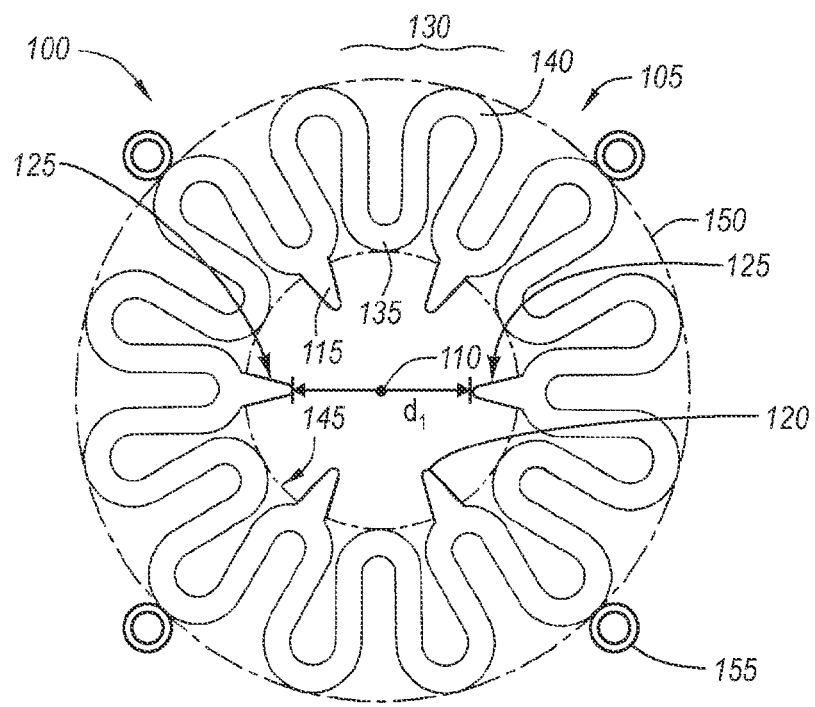
FIG. 1A is a top view of an example of a closure device in a deployed configuration.

It should be noted that the figures are not drawn to scale and that elements of similar structures or functions are generally represented by like-reference numerals for illustrative purposes throughout the figures. It also should be noted that the figures are only intended to facilitate the description of examples of the present invention.

DETAILED DESCRIPTION

Devices and methods are disclosed herein for managing access through tissue. In particular, several examples are described below in which a closure device may be deployed to close an opening in a body lumen. At some point after the device has been deployed to close the opening in the body lumen, such as after the hole in the body lumen has healed, it may be desirable to remove the closure device. In at least one example, the closure device includes device-capture features. The device-capture features may provide access points for an external device to engage the closure device for removal from the patient as desired. Alternatively, the device-capture features may provide access points usable to move, reposition, or expand the closure device to provide access to the body lumen while maintaining the closure device, or at least a portion of the closure device, within the patient. For instance, the closure device can be expanded sufficiently to allow a guidewire, catheter, introducer sheath or other medical instrument access through skin, tissue, body lumen, etc. Additional information regarding the functionality and capabilities of a closure device usable to gain medical instrument access subsequent to an initially performed medical procedure can be found in U.S. patent application Ser. No. 11/767,818, filed Jun. 25, 2007, entitled "Methods, Devices, and Apparatus for Managing Access Through Tissue", the disclosure of which is incorporated by reference herein in its entirety. Several examples of closure devices with several configurations of device-capture features as well as methods for removing closure devices are also described in more detail below.

Turning now to the drawings, FIGS. 1A-1D show a first example of a closure device 100 for managing access through tissue. The closure device 100 may be used for closing an incision, puncture, or other passage through tissue. In some examples, the closure device 100 may close communication with a blood vessel or other body lumen (not shown). The closure device 100 may include a body 105. In the present example, the body 105 may be generally annular in shape and/or may surround a central axis 110. As used herein, an "annular-shaped body" may include any hollow body, e.g., including one or more structures surrounding an opening, whether the body is substantially flat or has a significant thickness or depth. Thus, although an annular-shaped body may be circular, it may include other noncircular shapes as well, such as elliptical or other shapes that are asymmetrical about a central axis. In other examples, the body 105 may include other shapes and/or may not have a central axis 110. In some examples, the shape of the body 105 can be shaped according to how the arteriotomy is shaped upon dilation.

The closure device 100 for managing access through tissue may include a plurality of tissue-engaging portions 115 extending from the body 105. The tissue-engaging portions 115 may include edges 125 and/or tip portions 120. Portions of the tissue-engaging portions 115 may include tip portions 120 that are sharp and/or obtuse. Parts of the tissue-engaging portions 115 also include edges 125. In some examples, the tissue-engaging portions 115 may not have edges such that they are generally rounded.

In the present example, the tip portions 120 may be obtuse to facilitate engaging the tissue. In some examples where the tip portion 120 is obtuse, the tip portion 120 may not substantially penetrate the tissue, but rather may engage the tissue to manage access through the tissue. For example, if the closure device 100 for managing access through tissue were used with an opening in a body lumen, the tip portions 120 may not penetrate through the tissue into the body lumen, but rather may engage the tissue near the opening (although in some examples, the tip portions 120 may partially penetrate the tissue). Engaging tissue may include using frictional forces and/or other forces to manipulate the tissue. For example, in an example where the tissue-engaging portions 115 have tip portions 120 that are obtuse, the tip portions 120 may engage the tissue such that, as the closure device 100 moves back toward the deployed configuration, the tissue is pulled closed. In other examples, the tip portion 120 may substantially penetrate the tissue. In further examples, the tip portions 120 of primary tissue-engaging portions (not shown) may substantially penetrate the tissue while the tip portions 120 of secondary tissue-engaging portions (not shown) may not substantially penetrate the tissue. Other configurations of the tissue-engaging portions 115 and their tip portions 120 may be used.

In the present example, the body 105 may include a plurality of looped or curved elements 130 that may be connected to one another to form the body 105. Each looped element 130 may include an inner or first curved region 135 and an outer or second curved region 140. The first and second curved regions 135, 140 may be out of phase with one another and/or may be connected alternately to one another, thereby defining an endless sinusoidal pattern. Alternatively, other generally zigzag patterns may be provided that repeat periodically, e.g., saw tooth or square tooth patterns (not shown), instead of a sinusoidal pattern, thereby defining inner and outer regions that may alternate about the body 105.

FIG. 1A shows the closure device 100 in a deployed configuration. In the present example, when the closure device 100 is in the deployed configuration, the first curved regions 135 may define an inner periphery 145 of the body 105 and the closure device 100, and the second curved regions 140 may define an outer periphery 150. Regardless of the configuration of the device, the closure device 100 includes device-capture features 155.

The device-capture features 155 are secured to one or more of the curved elements 130. In addition, the device-capture features 155 may be located within or on the inner periphery 145 and/or outside of or on the outer periphery 150. Further, any number of device-capture features 155 may be located at the described locations and/or at other locations on the closure device 100. In the illustrated example, the device-capture features 155 are located on several of the curved regions 140. The device-capture features 155 allow the closure device 100 to be disengaged from tissue to allow the closure device 100 to be removed, moved, repositioned, or generally manipulated. The deployment of the closure device 100 will first be discussed, followed by a discussion of alternative configuration of devices with device-capture features.

The plurality of tissue-engaging portions 115 may be biased to extend towards one another. In the present example, the tissue-engaging portions 115 may be biased generally inwardly into the space bounded by the inner periphery 145. In other configurations, the tissue-engaging portions 115 may be biased toward the central axis 110. In other examples, at least two of the tissue-engaging portions 115 may be biased to extend towards each other.

In the present example, the tissue-engaging portions 115 may be disposed on the first curved regions 135 and/or oriented toward the central axis 110 when the closure device 100 is in the deployed configuration. The tissue-engaging portions 115 may be provided in pairs opposite from one another, as in the present example. The tissue-engaging portions 115 may be provided symmetrically with respect to the central axis 110 and/or may be provided asymmetrically.

Additionally, as shown in FIGS. 1A-1D, the tissue-engaging portions 115 may be disposed on alternating first curved regions 135. Thus, at least one period of a zigzag pattern may be disposed between adjacent tissue-engaging portions 115, which may enhance flexibility of the closure device 100, as explained further below.

Figure 1B:
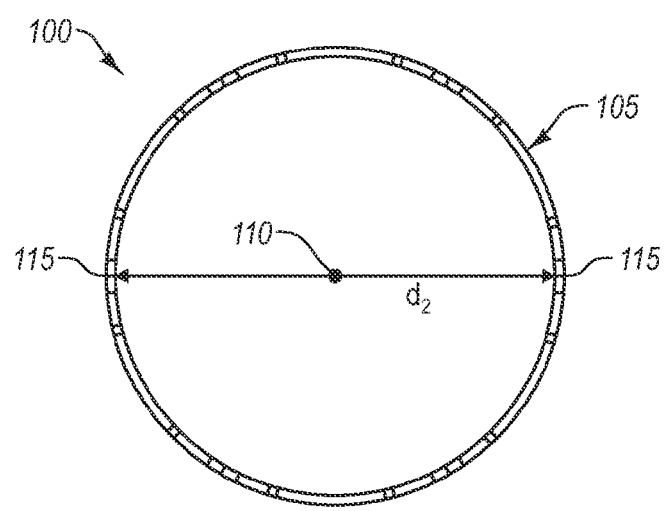
FIG. 1B is a top view of the example shown in FIG. 1A of a closure device in a deployed configuration.
Figure 1C:
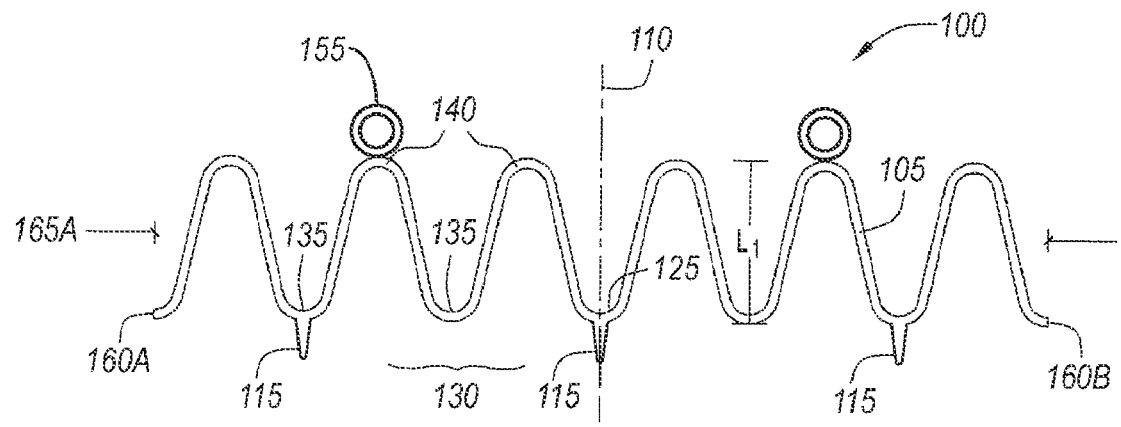
FIGS. 1C and 1D are side views of the example of the closure device, with the tissue-engaging portions oriented substantially transversely from the planar orientation, in compressed and expanded states, respectively.

In the deployed configuration, shown in FIG. 1A, the tissue-engaging portions 115 may be separated by a first distance, i.e., $d_1$. FIGS. 1B and 1C illustrate the device in a pre-deployed configuration. In the pre-deployed configuration, the tissue-engaging portions 115 and the inner curved regions 135 of the body are rotated out of plane relative to the configuration illustrated in FIG. 1B. As shown in FIG. 1B, the body 105 and/or the tissue-engaging portions 115 may be deflected into the pre-deployed configuration. In the present example, the tissue-engaging portions 115 may extend transversely with respect to a plane defined in the deployed configuration, thereby defining the pre-deployed configuration for the closure device 100.

In other examples, the body 105 and/or the tissue-engaging portions 115 in the pre-deployed configuration may not extend transversely with respect to a plane defined in the deployed configuration. For example, the body 105 and/or the tissue-engaging portions 115 in the pre-deployed configuration may remain in a plane defined in the deployed configuration. In another example, the body 105 and/or the tissue-engaging portions 115 in the pre-deployed configuration may move out of, optionally not completely transverse to, a plane defined in the deployed configuration.

In the pre-deployed configuration, shown in FIG. 1B, the tissue-engaging portions 115 may be separated by a second distance, i.e., $d_2$. In the present example, the first distance $d_1$ (FIG. 1A) and the second distance $d_2$ (FIG. 1B) may be measured from the tip portions 120 of two tissue-engaging portions 115. In other examples, the first and second distances $d_1$, $d_2$ may be measured from another portion of the tissue-engaging portions 115, for example from the base (not shown) of the tissue-engaging portions 115. The first distance $d_1$, in the present example, may be smaller than the second distance $d_2$, such that the distance $d_1$ in the deployed configuration may be smaller than the distance $d_2$ in the pre-deployed configuration.

The distances $d_1$, $d_2$ may vary before deployment, pre-deployment, and/or when providing access through the tissue post deployment. With continued reference to FIGS. 1B-1C, before being deployed in tissue, the closure device 100 for managing access through tissue may be substantially in the pre-deployed configuration such that two tissue-engaging portions 115 may be separated by about the second distance $d_2$. When deployed in tissue, the closure device 100 may be substantially in the deployed configuration illustrated in FIG. 1A such that the two tissue-engaging portions 115 may be separated by about the first distance $d_1$.

In the present example, the tissue-engaging portions 115 may be oriented substantially parallel to the central axis 110 in the pre-deployed configuration, as shown in FIG. 1C. In this pre-deployed configuration, the body 105 may have a generally annular shape defining a length, 11, which may extend generally parallel to the central axis 110, and may correspond generally to an amplitude of the zigzag pattern. The body 105 may be sufficiently flexible such that the closure device 100 may assume a generally circular or elliptical shape, as shown in FIG. 1B, e.g. substantially conforming to an exterior surface of a delivery device (not shown) used to deliver the closure device 100 for managing access through tissue.

The tissue-engaging portions 115 and/or body 105 may be biased to move from the pre-deployed configuration towards the deployed configuration of FIG. 1A. Thus, with the tissue-engaging portions 115 in the pre-deployed configuration, the tissue-engaging portions 115 may penetrate and/or be engaged with tissue at a puncture site. When the closure device 100 is released, the tissue-engaging portions 115 may attempt to return towards one another (i.e., the distance may decrease from the second distance $d_2$ toward the first distance $d_1$) as the closure device 100 moves towards the deployed configuration, thereby drawing the engaged tissue together and substantially closing and/or sealing the puncture site, as explained further below.

The looped elements 130 may distribute stresses in the closure device 100 for managing access through tissue as the device moves between the deployed and pre-deployed configurations, thereby generally minimizing localized stresses that may otherwise plastically deform, break, and/or otherwise damage the closure device 100 during delivery. In addition, when the closure device 100 is in the pre-deployed configuration, the looped elements 130 may be movable between a compressed state, such as that shown in FIG. 1D, and an expanded state, such as that shown in FIG. 1C (where opposite ends 160a, 160b are connected to one another). The body 105 may be biased towards the expanded state, but may be compressed to the compressed state, e.g., by constraining the closure device 100. Alternatively, only a portion of the body 105 may be biased towards the expanded state. For example, in the present example, the first curved regions 135 and/or the looped elements 130 may be biased towards the compressed state. Furthermore, the looped elements 130 may reduce the force required to be exerted on the closure device 100 to transition the closure device 100 from the deployed configuration to the pre-deployed configuration before loading onto a delivery device (not shown).

Figure 1D:
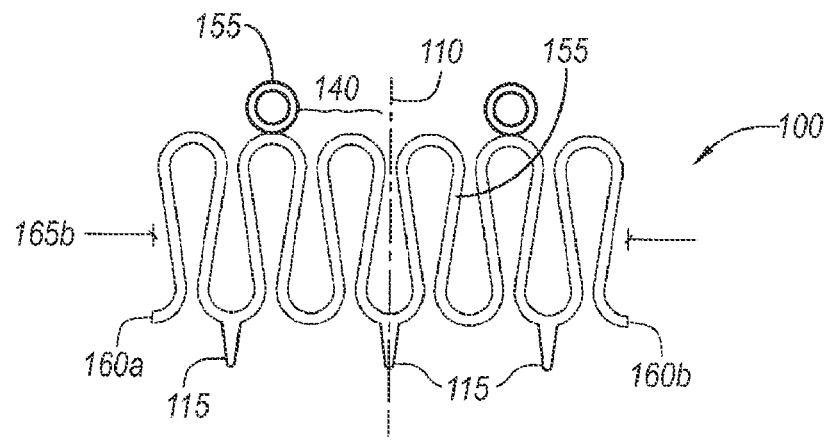
Figure 1E:
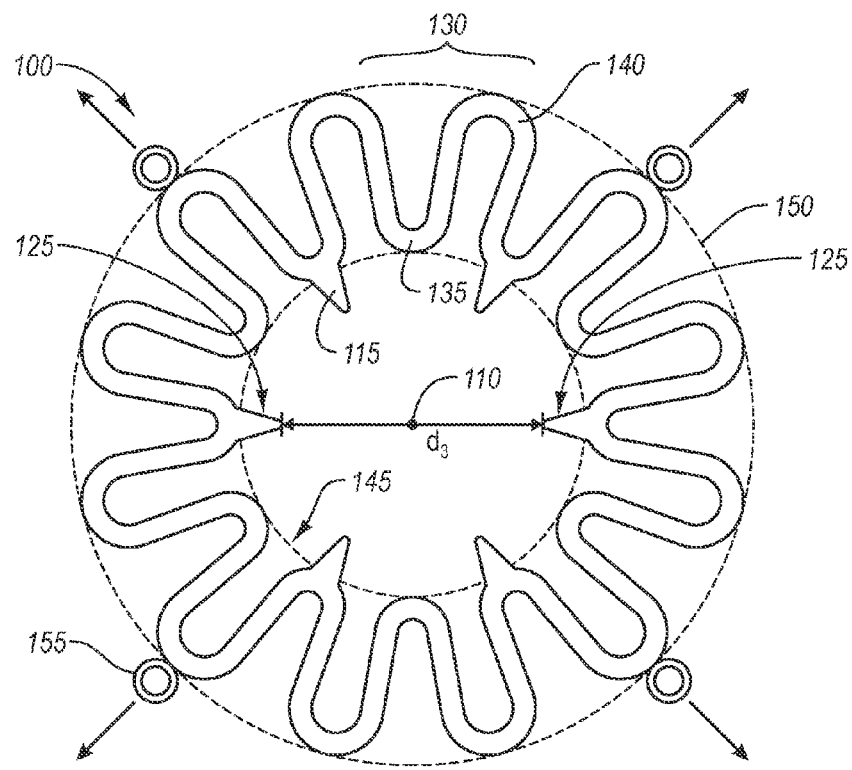
FIG. 1E is an example of the closure device in which the tissue-engaging portions are drawn from contact with the tissue.

With the closure device 100 in the pre-deployed configuration, the looped elements 130 may be circumferentially and/or radially compressed to the compressed state until the closure device 100 defines a first diameter or circumference 165a, such as that shown in FIG. 1D. The closure device 100 may be constrained in the compressed state, e.g., by loading the closure device 100 onto a carrier assembly or a delivery device (not shown), as described further below. When released from the constraint, e.g., when deployed from the carrier assembly, the closure device 100 may automatically expand towards the expanded state, such as that shown in FIG. 1C, thereby defining a second diameter or circumference 165b. Thus, the curved elements 130 may facilitate reducing the profile of the closure device 100 during delivery, e.g., to facilitate introducing the closure device 100 through a smaller puncture or passage. Once the closure device 100 is deployed entirely from the delivery device, the looped elements 130 may resiliently expand as the closure device 100 returns towards the deployed configuration.

After the closure device 100 is deployed, it may be desirable to remove the closure device 100. For example, it may be desirable to remove the closure device 100 once the tissue has healed that was closed by the closure device 100. As previously introduced, the device-capture features 155 facilitate removal of the closure device.

FIG. 1D illustrates the closure device 100 being expanded to draw the tissue-engaging portions 115 from engagement with tissue. In particular, as illustrated in FIG. 1D the device-capture features 155 may each be moved away from the central axis 110. The device-capture features 155 are secured to the looped elements 130. Accordingly, as the device-capture features 155 are moved away from the central axis 110, the curved elements 130, including the tissue-engaging portions 115, are also drawn away from the central axis 110. The distance the device-capture features 155 move may result in the tissue-engaging portions 115 being at a distance from each other that is larger than distance $d_1$ illustrated in FIG. 1A, corresponding to the distance between the tissue-engaging portions 115 at a deployed state.

The distance the device-capture features 155 moves may be sufficient for the tissue-engaging portions 115 to be drawn from engagement with the tissue. Once the tissue-engaging portions 115 are drawn from engagement with the tissue, the closure device 100 may be moved parallel to the central axis 110. Movement of the device-capture features parallel to the central axis 110 may cause the closure device 100 to return toward the pre-deployment position in which the curved elements 130 are generally parallel to the central axis 110. Accordingly, the device-capture features 155 facilitate the removal of the closure device 100 after the closure device 100 has been deployed.

Additionally, the device-capture features 155 may be configured to allow a practitioner to locate the device-capture features 155. For example, the device-capture features 155 may include radiopaque markers or other markers visible using external imaging, such as fluoroscopy and/or ultrasound. In at least one example, the closure device 100 may be coated with radiopaque material, which may be a high-density material such as gold, platinum, platinum/iridium, and the like.

Alternatively, a closure device 100 may be partially coated with radiopaque material by using masking techniques. For example, the entire closure device 100 may first be coated with radiopaque material. The closure device 100 may then be masked at locations where the radiopaque coating is desired. For example, the looped elements 30 of the closure device 100 may be left unmasked during this process if it is desired to leave the looped elements 30 uncoated by radiopaque material. This may be desirable, e.g., to prevent radiopaque material from adversely affecting the flexibility of the body 105. The closure device 100 may then be treated to remove the radiopaque material from the unmasked areas, in this example, the body 105. The masking may then be removed using conventional processes, leaving the rest of the closure device 100 coated with radiopaque material, including the device-capture features 155.

In some examples, the device 100 may include a bioactive agent. The bioactive agent may be associated with a base coat and/or top coat and/or incorporated or otherwise applied to a supporting structure of the closure device 100.

The bioactive agent may have any therapeutic effect. Examples of suitable therapeutic properties may include anti-proliferative, anti-inflammatory, antiplatelet, anti-coagulant, anti-fibrin, antithrombonic (check spelling), antimitotic, antibiotic, antiallergic, antioxidant properties, and/or other therapeutic properties.

For example, a bioactive agent may be used to reduce scar tissue response when the closure device 100 is deployed in tissue. Reducing scar tissue response, structural tissue response, restenosis, and/or thrombosis may facilitate access to the tissue after the closure device 100 is deployed. For example, if a device did not use a beneficial agent to reduce scar tissue response, structural tissue response, restenosis, and/or thrombosis after deployment, these and/or other tissue responses may hinder future access to the tissue.

In some examples, silver and/or alloys of silver may be incorporated into at least a portion of the closure device 100. For example, silver and/or alloys of silver may be included as a component of a mixture that may be incorporated into the material of the closure device 100. In examples where a closure device 100 is formed from a sheet of material, the sheet of material may include silver and/or alloys of silver as a component of the material. In examples where the closure device 100 is formed from a wire as described in U.S. Pat. No. 6,719,777, the wire may include silver and/or alloys of silver as a component of the wire.

In other examples, at least a portion of the closure device 100 may include a coating that includes silver and/or alloys of silver as a component of the coating. For example, a coating of silver and/or alloys of silver may be applied to a portion of the surface of the closure device 100. Coatings may be applied using various coating methods. Coating methods may include physical vapor deposition, chemical vapor deposition, ion beam assisted deposition, electroplating and/or other coating methods. Physical vapor deposition may include sputter deposition and/or other physical vapor deposition methods.

Figure 2:
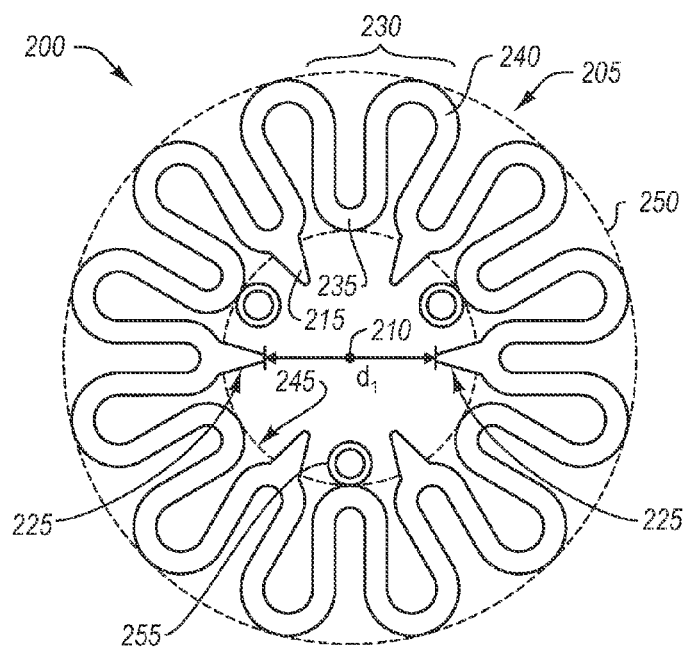
FIG. 2 is a top view of another example of a closure device according to one example.

FIG. 2 illustrates a device 200 similar to the closure device 100 illustrated in FIGS. 1A-1D in which similar parts have similar numbers that are increased by 100. Accordingly, the device 200 illustrated in FIG. 2 includes a body 205 having tissue engagement portions 215 disposed generally curved regions 235 of curved elements 230. Device-capture features 255 are also secured to the curved regions 235 of the curved elements. As illustrated in FIG. 2, the device-capture features 255 are located generally about an inner periphery 245.

Figure 3:
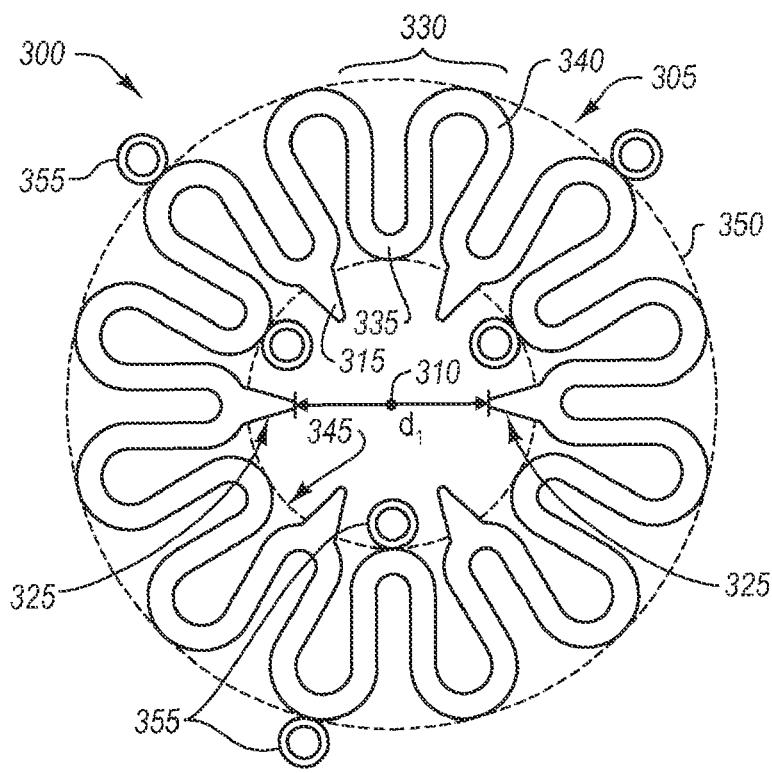
FIG. 3 is a top view of another example of a closure device according to one example.

FIG. 3 illustrates an alternative example in which the device-capture features 355 are secured to a combination of curved regions 335 and curved regions 340 of curved elements 330. As a result, device-capture features 355 are disposed generally about an inner periphery 345 as well as about an outer periphery 350. As will be discussed in more detail below, device-capture features may be secured to inner portions and/or outer portions as well as other portions of devices having various configurations as described below. Regardless of the configuration of the devices and the configuration of the device-capture features, device-capture features allow devices to be removed from engagement with tissue after the devices have been deployed. More generally, the device-capture features allow a closure device to be removed, moved, repositioned, or generally manipulated.

Figure 4:
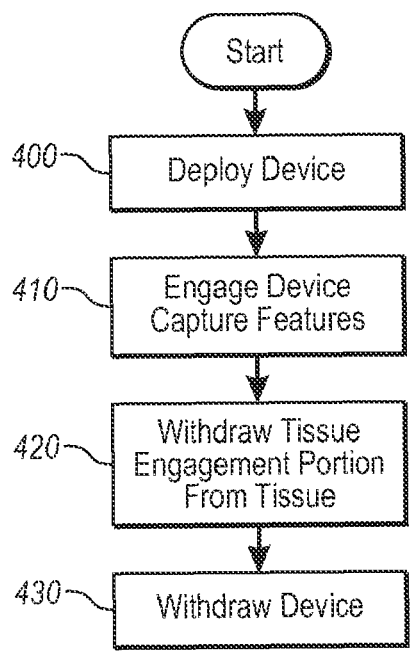
FIG. 4 is a flowchart summarizing one example of a method of removing a closure device according to one example.

FIG. 4 summarizes one example of a method for removing a device with device-capture features. It will be understood that a similar method may be used to move, reposition, or generally manipulate the closure device. As illustrated in FIG. 4, the method begins at step 400 with deployment of a device having device-capture features. In one example, a deployment device may be used to deploy the device in a similar manner as described above. As previously introduced, at some point it may be desirable to remove the device, such as after the tissue the device is engaging has healed. While a removal process is described herein, it will be appreciated that the device may be left in engagement with the tissue indefinitely.

To remove the device the method continues at step 410 when an external device engages the device-capture features. In at least one example, a removal device can engage the device. Engaging the external device can include initially locating the device and introducing a distal end of the removal device into proximity with the device and into proximity with the engagement points in particular.

Once the device-capture features have been engaged, at step 420 the device-capture features are moved to cause tissue engagement portions to be withdrawn from engagement with the corresponding tissue. In at least one example, moving the device to cause the tissue engagement portions to be withdrawn from engagement with tissue includes moving the device-capture features in such a manner as to cause the device to return toward a pre-deployed position. This movement may include moving the device-capture features away from a central axis of the device and/or moving the device-capture features parallel to the central axis. Once the tissue-engaging portions are withdrawn from engagement with the tissue, the device may be withdrawn at step 430.

Accordingly, the method provides for removal of devices with device-capture features after the devices have been deployed. Such a method may be performed on devices having any number of body configurations as well as device-capture features. Several device configurations will now be discussed below that include device-capture features coupled thereto. The devices illustrated and discussed below include device-capture features that are located toward outer peripheries of the devices. It will be appreciated that such configurations are provided only to illustrate various device configurations and that device-capture features may be provided at other locations on the device, such as toward, within, and/or on the inner periphery and in combinations in which device-capture features are located both toward, within, on, and/or outside of the outer periphery of the device. Further, it will be appreciated that device-capture features may also be secured to the body by intermediate members as well as by any other suitable structure.

Figure 5A:
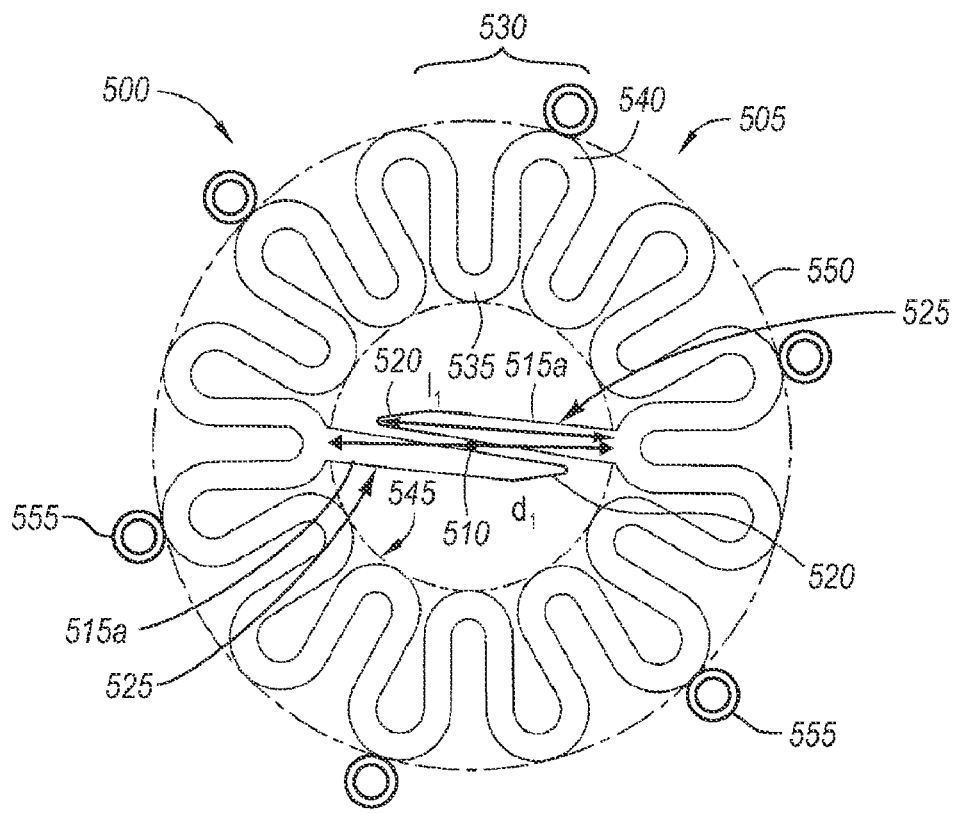
FIGS. 5A-5B illustrate another example of a closure device including a pair of primary tissue-engaging portions.
Figure 5B:
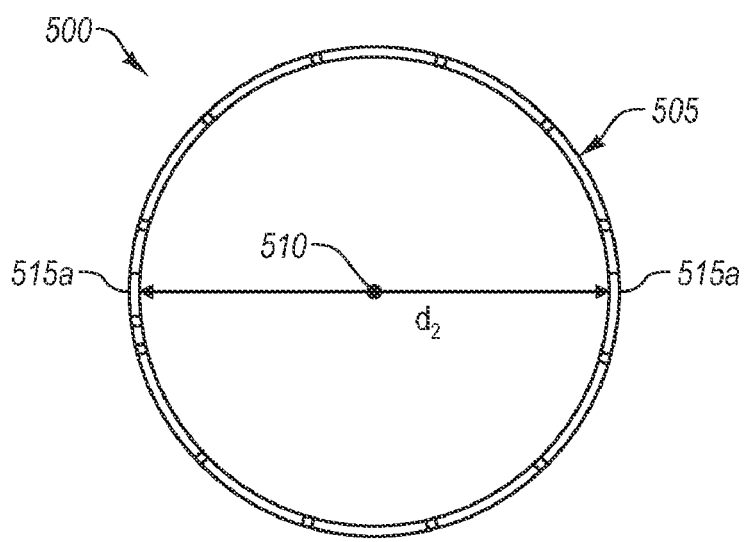

FIGS. 5A-5B illustrate another example of a closure device 500 that includes device-capture features 555. The closure device 500 may include a generally annular shaped body 505 defining a plane and disposed about a central axis 500 extending through the plane. The body 505 may include a plurality of looped elements 530 that are connected to one another to form the body 505, similar to the example of FIGS. 1A-1E. Each looped element 530 may include an inner or first curved region 535 and an outer or second curved region 540, in a deployed configuration (shown in FIG. 5A). Similar to the example of FIGS. 1A-1D, the first and second curved regions 535, 540 may form an endless sinusoidal pattern or other generally zigzag pattern. When the closure device 500 is in the deployed configuration, which may be substantially planar in the present example, as shown in FIG. 5A, the first curved regions 535 may define an inner periphery 545, and the second curved regions 540 may define an outer periphery 550.

Unlike the previous example, the closure device 500 for managing access through tissue of the present example may include only one pair of primary tissue-engaging portions 515a. The primary tissue-engaging portions 515a may have a length 11, although alternatively each of the primary tissue-engaging portions 515a may have a different length than one another.

Although the length, $l_1$, is illustrated as extending from a curved region 535, 540, beyond the central axis 510, it may be possible for the length, $l_1$, to be less than this distance, such as a length defined from a curved region 535, 540 to the central axis 510 or a length defined from a curved region 535, 540 toward, but not passing the central axis 510. The primary tissue-engaging portions 515a may be disposed in one or more opposing pairs, e.g., on opposing first curved regions 535, and may be oriented towards and/or across the central axis 510 in the planar configuration. In the deployed configuration, the primary tissue-engaging portions 515a may be sufficiently long such that the primary tissue-engaging portions 515a at least partially overlap one another, i.e., extend across the central axis 510 towards an opposing tissue-engaging portion 515a. Therefore, the tip portions 520 of the primary tissue-engaging portions 515a may extend past the central axis 500 and/or the primary tissue-engaging portions 515a in each pair may lie substantially parallel to each other when the closure device 500 for managing access through tissue is in the deployed configuration. Each of the primary tissue-engaging portions 515a may include a variety of tip portions 520 and/or edges 525.

In the deployed configuration, shown in FIG. 5A, the primary tissue-engaging portions 515a may be separated by a first distance, i.e., $d_1$. In a pre-deployed configuration, shown in FIG. 5B, the primary tissue-engaging portions 515a may be separated by a second distance, i.e., $d_2$. In the present example, the first and second distances $d_1$, $d_2$ may be measured from the base (not shown) of the two primary tissue-engaging portions 515a. In other examples, the first and second distances $d_1$, $d_2$ may be measured from another portion of the primary tissue-engaging portions 515a, for example from tip portion 520 of the primary tissue-engaging portions 515a. The first distance $d_1$, in the present example, may be smaller than the second distance $d_2$, such that the distance $d_1$ in the deployed configuration may be smaller than the distance $d_2$ in the pre-deployed configuration.

The distances $d_1$, $d_2$ may vary before deployment, pre-deployment, and/or when providing access through the tissue post deployment. In the present example, before being deployed in tissue, the closure device 500 for managing access through tissue may be substantially in the pre-deployed configuration such that the two primary tissue-engaging portions 515a may be separated by about the second distance $d_2$. When deployed in tissue, the closure device 500 may be substantially in the deployed configuration such that the two primary tissue-engaging portions 515a may be separated by about the first distance $d_1$. When providing access to the tissue after being deployed in tissue, the closure device 500 may be moved from the substantially deployed configuration toward and/or to the pre-deployed configuration.

As shown in FIG. 5B, the body 505 and/or the primary tissue-engaging portions 515a may be deflected into the pre-deployed configuration, similar to the example of FIGS. 1A-1D. In the present example, the primary tissue-engaging portions 515a may extend transversely with respect to a plane defined in the deployed configuration, thereby defining the pre-deployed configuration for the closure device 500.

The primary tissue-engaging portions 515a and/or body 505 may be biased to move from the pre-deployed configuration towards the deployed configuration of FIG. 5A. Thus, with the primary tissue-engaging portions 515a in the pre-deployed configuration, the primary tissue-engaging portions 515a may penetrate and/or be engaged with tissue at a puncture site. When the closure device 500 is released, the primary tissue-engaging portions 515a may attempt to return towards one another (i.e., the distance may decrease from the second distance $d_2$ toward the first distance $d_1$) as the closure device 500 moves towards the deployed configuration, thereby drawing the engaged tissue together and substantially closing and/or sealing the puncture site, as explained further below.

The primary tissue-engaging portions 515a of the present example may include the tip portions 520 and/or edges 525. For example, the tip portions 520 and/or edges 525 of the primary tissue-engaging portions 515a, in the present example, may be obtuse.

FIGS. 6A-6G illustrate a further example of a closure device 600 for managing access through tissue according to the present invention. In the present example, the device 600 may include a body 605. The body may include looped elements 630 and tissue-engaging portions 615, similar to the previous examples. The reference numbers for elements of the device 600 are consistent with like elements used for the devices 100, 200, 300, and 500.

The device 600 for managing access through tissue of the present example may include a plurality of primary tissue-engaging portions 615a and a plurality of secondary tissue-engaging portions 615b. Each of the primary and secondary tissue-engaging portions 615a, 615b may include a variety of tip portions 650 and/or edges 625.

The primary tissue-engaging portions 615a may be similar to the primary tissue-engaging portions 515a of the previous example. However, each of the secondary tissue-engaging portions 615b may be disposed on a first or inner curved region 605, such that one or more secondary tissue-engaging portions 615b may be provided between opposing pairs of primary tissue-engaging portions 615a. Each of the secondary tissue-engaging portions 615b may have a length $l_2$ that is substantially less than the length, $l_1$, of the primary tissue-engaging portions 615a.

Although the length, $l_1$, is illustrated as extending from a curved region 635, 640, beyond the central axis 610, it may be possible for the length, $l_1$, to be less than this distance, such as a length defined from a curved region 635, 640 to the central axis 610 or a length defined from a curved region 635, 640 toward, but not passing the central axis 610. A secondary tissue-engaging portion 615b may be disposed on either side of each primary tissue-engaging portion 615a in the present example. For example, the device 600 for managing access through tissue may include first and second primary tissue-engaging portions 615a. Each of the first and second primary tissue-engaging portions 615a may include a secondary tissue-engaging portion 615b on either side of it. Thus, the device 600 may include a total of two primary tissue-engaging portions 615a and four secondary tissue-engaging portions 615b. The secondary tissue-engaging portions 615b, in the present example, may be disposed substantially symmetrically about the central axis 610. The tissue-engaging portions 615a, 615b may be provided on every other first curved regions 605. For example, a first curved region 605 having neither a primary tissue-engaging portion 615a nor a secondary tissue-engaging portion 615b may separate each adjacent tissue-engaging portion, e.g., between two adjacent secondary tissue-engaging portions 615b, or between a secondary tissue-engaging portion 615b and a primary tissue-engaging portion 615a. The primary and secondary tissue-engaging portions 615a, 615b may also include other orientations and arrangements.

Figure 6A:
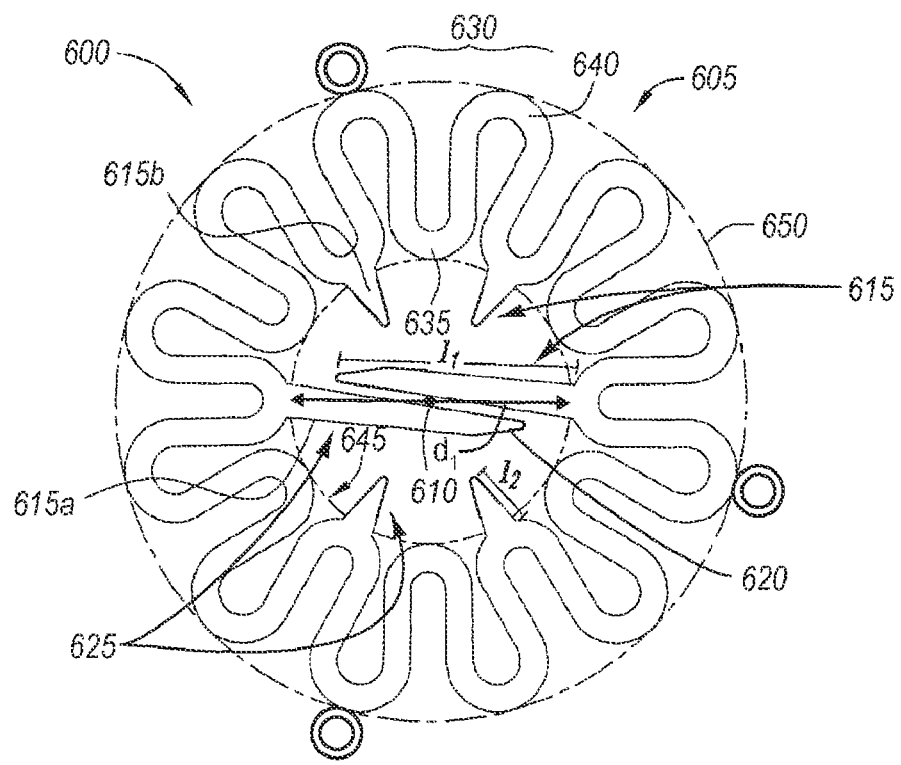
FIGS. 6A-6D illustrate further examples of a closure device including primary tissue-engaging portions and secondary tissue-engaging portions.
Figure 6B:
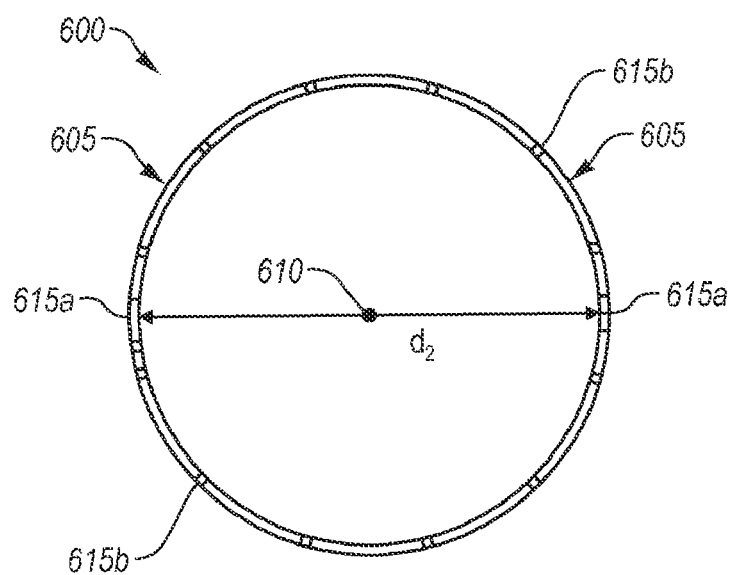
Figure 6C:
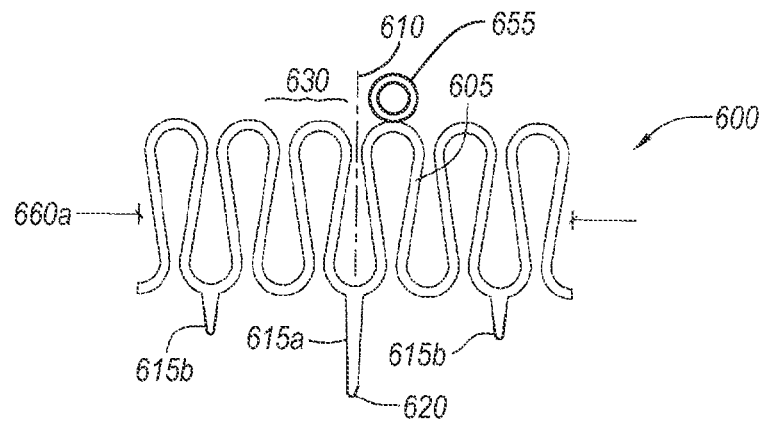
Figure 6D:
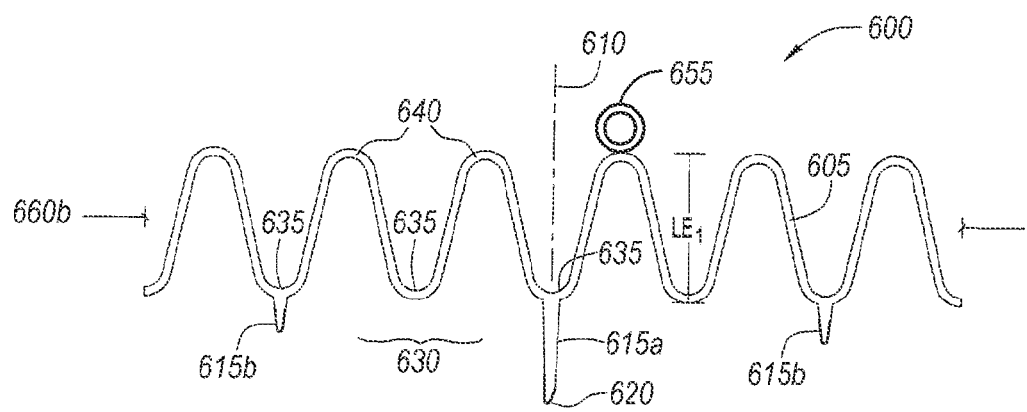

The device 600 may be moved from the deployed configuration of FIG. 6A to the pre-deployed configuration, as shown in FIGS. 6B-6D. In the present example, the body 605 and/or the tissue-engaging portions 615a, 615b may be deflected into the pre-deployed configuration such that they extend transversely with respect to the plane defined in FIG. 6A. The primary tissue-engaging portions 615a and/or secondary tissue-engaging portions 615b may be oriented substantially parallel to the central axis 610 in the pre-deployed configuration, as shown in FIGS. 6B-6D. In the pre-deployed configuration of the present example, the body 605 may have a generally annular shape defining a length, $LE_1$, which extends generally parallel to the central axis 610, and corresponds generally to an amplitude of the sinusoidal pattern. The body 605 may be sufficiently flexible such that the device 600 may assume a generally circular or elliptical shape, as shown in FIG. 6B, e.g., conforming to an exterior surface of a delivery device (not shown).

The tissue-engaging portions 615a, 615b may be biased towards one another and/or towards the central axis 610, i.e., due to the bias of the device 600 towards the deployed configuration of FIG. 6A. With the device 600 in the pre-deployed configuration, the device 600 may be delivered such that the primary tissue-engaging portions 615a, in the present example, may entirely penetrate the wall of a blood vessel or other body lumen, while the secondary tissue-engaging portions 615b may only partially penetrate and/or engage the wall due to their relative lengths. In other examples, the primary tissue-engaging portions 615a may partially penetrate the wall of a blood vessel or other body lumen, while the secondary tissue-engaging portions 615b may partially penetrate and/or engage the wall due to their relative lengths. In further examples, the primary tissue-engaging portions 615a may engage the wall of a blood vessel or other body lumen, while the secondary tissue-engaging portions 615b may penetrate and/or engage the wall due to their relative lengths.

In the deployed configuration, shown in FIG. 6A, the primary tissue-engaging portions 615a may be separated by a first distance, i.e., $d_1$. In a pre-deployed configuration, shown in FIG. 6B, the primary tissue-engaging portions 615a may be separated by a second distance, i.e., $d_2$. In the present example, the first and second distances $d_1$, $d_2$ may be measured from the base (not shown) of the two primary tissue-engaging portions 615a. In other examples, the first and second distances $d_1$, $d_2$ may be measured from another portion of the primary tissue-engaging portions 615a, for example from the tip portions 620 of the primary tissue-engaging portions 615a. The first distance $d_1$, in the present example, may be smaller than the second distance $d_2$, such that the distance $d_1$ in the deployed configuration may be smaller than the distance $d_2$ in the pre-deployed configuration.

The distances $d_1$, $d_2$ may vary before deployment, pre-deployment, and/or when providing access through the tissue post deployment. In the present example, before being deployed in tissue, the device 600 for managing access through tissue may be substantially in the pre-deployed configuration such that the two primary tissue-engaging portions 615a may be separated by about the second distance $d_2$. When deployed in tissue, the device 600 may be substantially in the deployed configuration such that the two primary tissue-engaging portions 615a may be separated by about the first distance $d_1$. When providing access to the tissue after being deployed in tissue, the device 600 may be moved from the substantially deployed configuration substantially toward and/or to the pre-deployed configuration.

The looped elements 630 may be expandable between a compressed state, as shown in FIG. 6C, and an expanded state, as shown in FIG. 6D, similar to the example of FIGS. 1C and 1D. The looped elements 630 may be biased to the expanded state, but may be resiliently compressed to the compressed state, e.g., by constraining the device 600.

As described in connection with FIG. 6A, each of the secondary tissue-engaging portions 615b may have a length $l_2$ that is substantially less than the length, $l_1$, of the primary tissue-engaging portions 615a. Although the length, $l_1$, in FIG. 6G is illustrated as extending from a curved region 605, 640, beyond the central axis 610, it may be possible for the length, $l_1$, to be less than this distance, such as a length defined from a curved region 605, 640 to the central axis 610 or a length defined from a curved region 605, 640 toward, but not passing the central axis 610, as described in connection with FIGS. 6A and 6E.

Figure 7:
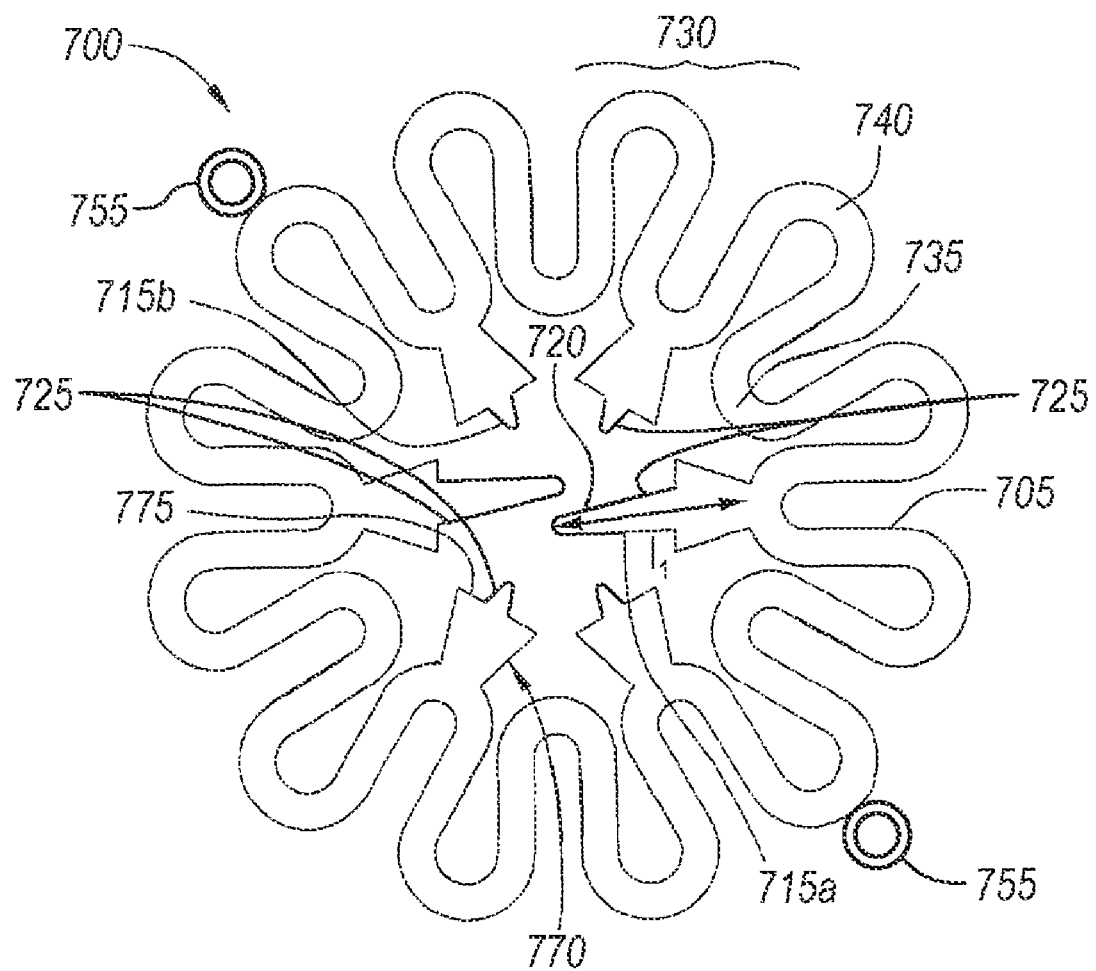
FIG. 7 illustrates another example of a closure device including stop members.

Turning to FIG. 7, another example of a device 700 is shown that, similar to the devices described above, may include a plurality of looped elements 730 that interconnect to form a body 705. One or more device-capture features 755 are secured to the body 705. For example, each looped element 730 may have a first or inner curved region 735 and a second or outer curved region 740. The device-capture features 755 may be secured to either or both of the curved regions 735, 740. Primary tissue-engaging portions 715a may be disposed on opposing first curved regions 735. Secondary tissue-engaging portions 715b may be provided on first curved regions 735 on either side of each primary tissue-engaging portion 715a. In addition, a first curved region 735 without a tissue-engaging portion 715a, 715b may separate adjacent tissue-engaging portions. Although the length, $l_1$, is illustrated as extending from a curved region 735, 740, beyond a central axis, it may be possible for the length, $l_1$, to be less than this distance, such as a length defined from a curved region 735, 740 to the central axis or a length defined from a curved region 735, 740 toward, but not passing the central axis.

The device 700 may also include stop members 770 on one or more of the tissue-engaging portions 715a, 715b, e.g., adjacent the respective first curved region 735. Each stop member 770 may be blunt-shaped. For example, the stop members 770 may be shaped generally triangularly with an apex 775 of the stop member 770 extending from the first curved region 735, and the tissue-engaging portion 715a, 715b extending from a wide or blunt base 775 of the stop member 770. During use, the blunt bases 775 may limit penetration of the respective tissue-engaging portions 715a, 715b into tissue by reducing an effective length of the respective tissue-engaging portion 715a, 715b. For example, when the tissue-engaging portions 715a, 715b are driven into tissue, the tissue-engaging portions 715a, 715b may penetrate the tissue until the blunt bases 775 contact the tissue, whereupon the tissue-engaging portions 715a, 715b may be prevented from penetrating further into the tissue. Stop members 770 may be used in other examples to decrease the amount of the tissue-engaging portion 715a, 715b that penetrates and/or engages surrounding tissue. Each of the tissue-engaging portions 715a, 715b may include a variety of tip portions 720 and/or edges 725.

FIGS. 8A-8E show a further example of a device 800 that includes device-capture features 855. The device 800 may include a peripheral body 805 and a plurality of tissue-engaging portions 815. Each tissue-engaging portion 815 may include a pair of legs 817 terminating in a tip portion 820. In the present example, the tissue-engaging portions 815 may be configured for penetrating and/or otherwise engaging tissue. Each of the tissue-engaging portions 815 may include a variety of tip portions 820 and/or edges 825. The tissue-engaging portions 815 may be disposed substantially symmetrically about a central axis 810. The body 805 may include a plurality of expandable elements 840 that may be connected by hinged regions 822. The hinged regions 822 may also connect adjacent tissue-engaging portions 815.

Figure 8A:
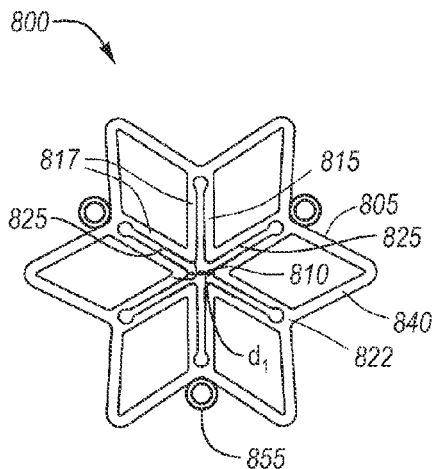
FIGS. 8A-8E illustrate a further example of a closure device.

FIG. 8A shows the device 800 in a deployed configuration. In the present example, the deployed configuration may be a substantially planar configuration. In other examples, the deployed configuration may be another type of configuration, as shown, for example, by the examples shown in FIGS. 17-20.

Figure 8B:
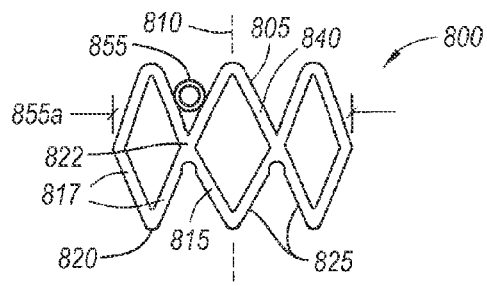
Figure 8C:
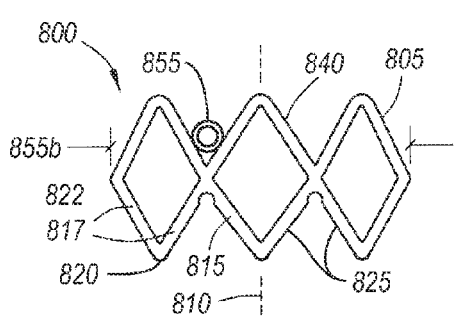
Figure 8D:
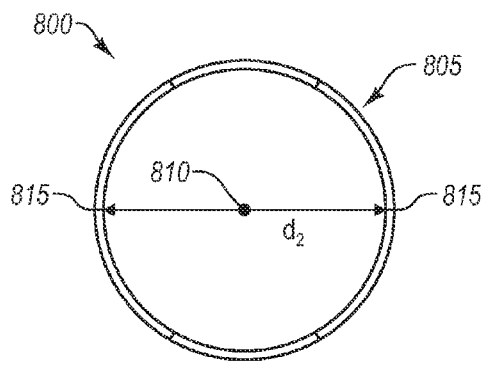

As shown in FIGS. 8B and 8D, the tissue-engaging portions 815 may be deflected such that they extend from the body 805 substantially transversely with respect to the plane defined by the device 800. In the examples of FIG. 8B-8D, the tissue-engaging portions 815 may be oriented substantially parallel to the axis 810 to define a pre-deployed configuration.

In the deployed configuration, shown in FIG. 8A, the tissue-engaging portions 815 may be separated by a first distance, i.e., $d_1$. In the pre-deployed configuration, shown in FIG. 8D, the tissue-engaging portions 815 may be separated by a second distance, i.e., $d_2$. In the present example, the first and second distances $d_1$, $d_2$ may be measured from a tip portion 820 of the tissue-engaging portions 815. In other examples, the first and second distances $d_1$, $d_2$ may be measured from another portion of the tissue-engaging portions 815, for example from the base (not shown) of the tissue-engaging portions 815. The first distance $d_1$, in the present example, may be smaller than the second distance $d_2$, such that the distance $d_1$ in the deployed configuration may be smaller than the distance $d_2$ in the pre-deployed configuration.

Figure 8E:
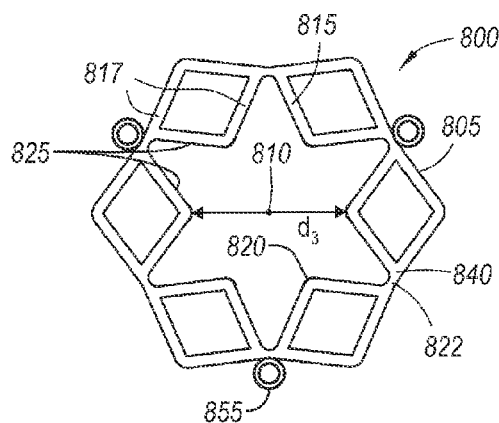

The tissue-engaging portions 815 may define an angle with respect to the axis 810, as shown in FIG. 8E, to define a removal configuration. The device 800 may move substantially toward a removal configuration after the device 800 has been deployed. In the present example, while in the removal configuration, the body 805 may have a generally annular shape, e.g., a hexagonal shape as shown in FIG. 8E. In other examples, the device 800 may take other shapes in the removal configuration.

In at least one example, the device-capture features 855 may be captured and moved away from the central axis 810 while maintaining the device 800 in substantially the same plane as when the device 800 is in the deployed configuration. In the removal configuration, the tissue-engaging portions 815 may be moved a sufficient distance to withdraw the tissue-engaging portions 815 from the tissue.

For example, in the removal configuration, the tissue-engaging portions 815 may be separated by a third distance, i.e., $d_3$. In the present example, the first and third distances $d_1$, $d_3$ may be measured from a tip portion 820 of the tissue-engaging portions 815. In other examples, the first and third distances $d_1$, $d_3$ may be measured from another portion of the tissue-engaging portions 815, for example from the base (not shown) of the tissue-engaging portions 815. The first distance $d_1$, in the present example, may be smaller than the third distance $d_3$, such that the distance $d_1$, in the deployed configuration may be smaller than the distance $d_3$ in the access configuration.

The removal configuration shown in FIG. 8E may provide an example of a removal configuration and/or pre-deployed that may be within the same plane as the deployed configuration. In other examples, a removal configuration and/or pre-deployed may extend away from a plane in the deployed configuration, though the pre-deployed configuration may not be transverse to the plane. In further examples, a removal configuration and/or pre-deployed configuration may both extend away from a plane in the deployed configuration, though the access and/or pre-deployed configuration may not be transverse to the plane, and away from a central axis 810.

The body 805 may be sufficiently flexible such that the device 800 may assume a generally circular or elliptical shape, as shown in FIG. 8D, e.g., conforming to an exterior surface of a delivery device (not shown) used to deliver the device 800.

In addition, the expandable elements 820 may be expandable from a compressed state, shown in FIG. 8B, to an expanded state, shown in FIG. 8C. The expandable elements 820 may be biased to the expanded state, but may be compressed to the compressed state, e.g., by constraining the device 800. In some examples, the device 800 may be formed with the expandable elements 820 in the expanded state.

With the closure device 100 in its pre-deployed configuration, the expandable elements 820 may be circumferentially and/or radially compressed to the compressed state such that the device 800 defines a first diameter 855a, shown in FIG. 8B. The device 800 may be constrained at the first diameter 855a, e.g., by loading the device 800 into a delivery device (not shown), as described further below. When released from the constraint, e.g., when deployed from the delivery device, the device 800 may automatically expand to a second diameter 855b, shown in FIG. 8C. Thus, the expandable elements 820 may reduce the profile of the device 800 for managing access through tissue during delivery, e.g., to facilitate introduction of the device 800 through a smaller puncture or other passage.

Although the lengths, $l_1$, are illustrated in FIGS. 8A-8C as extending from a curved region (not shown), beyond the central axis (not shown), it may be possible for the length, $l_1$, to be less than this distance, such as a length defined from a curved region to the central axis or a length defined from a curved region toward, but not passing, the central axis.

Figure 9:
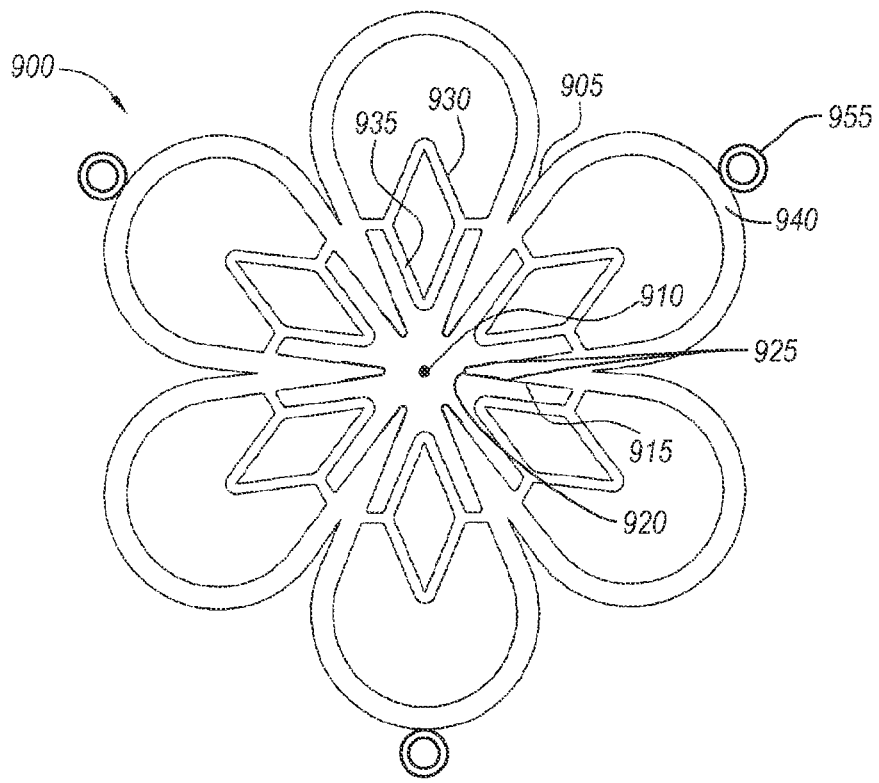
FIG. 9 illustrates an example of a closure device according to one example.

Turning to FIG. 9, another example of a closure device 900 for managing access through tissue according to the present invention is shown. The closure device 900 may include a body 905, a plurality of tissue-engaging portions 915, and/or a plurality of expandable elements 930 that may interconnect adjacent tissue-engaging portions 915. The body 905 may include outer curved regions 940 that may extend between adjacent tissue-engaging portions 915, thereby defining an outer periphery (not shown) for the closure device 900. The expandable elements 930, in the present example, may be spring elements.

The closure device 900 may be moveable between a deployed configuration, which is substantially planar in the present example, such as that shown in FIG. 9, and a pre-deployed configuration, which is substantially transverse to the deployed configuration in the present example. The closure device 900 may be biased towards the deployed configuration.

In the present example, the expandable elements 930 may generally be hollow diamond shaped elements, including curved inner regions 935 oriented towards the central axis 910 of the body 905 when the closure device 900 is in the deployed configuration. The expandable elements 930 may serve multiple purposes. One purpose may include biasing the closure device 900, e.g., allowing the closure device 900 to at least partially expand resiliently. For example, when the closure device 900 is deflected into the pre-deployed configuration (not shown), the expandable elements 930 may allow the tissue-engaging portions 915 to be moved away from the central axis 910 and/or one another. Thus, during deployment, the tissue-engaging portions 915 may be deflected radially outwardly or otherwise expanded to engage a larger area of tissue.

As the tissue-engaging portions 915 are expanded, the expandable elements 930 may deform to become wider (along a dimension extending generally between the adjacent tissue-engaging portions 915) and shorter (along a dimension extending generally parallel to the tissue-engaging portions 915). Once a force causing the tissue-engaging portions 915 to expand is removed, the expandable elements 930 may resiliently try to return towards their original shape, thereby pulling the tissue-engaging portions 915 substantially closer towards one another towards the deployed configuration.

Finally, after the closure device 900 is deployed, e.g., the tissue-engaging portions 915 have penetrated and/or engaged the tissue, the curved inner regions 935 may return towards the deployed configuration, and may pinch or otherwise engage tissue between the inner curved regions 935 and the adjacent tissue-engaging portions 915. Thus, contracting the expandable elements 930 may enhance the ability of the closure device 900 to seal a puncture site, e.g., by pulling engaged tissue inwardly towards the central axis 910 of the closure device 900.

After the closure device 900 has been deployed, the expandable elements 930 may be expanded by applying a force to the device-capture features 955 as described above. Accordingly, the device-capture features 955 allow the closure device 900 to be removed, moved, repositioned, or generally manipulated after deployment.

Figure 10:
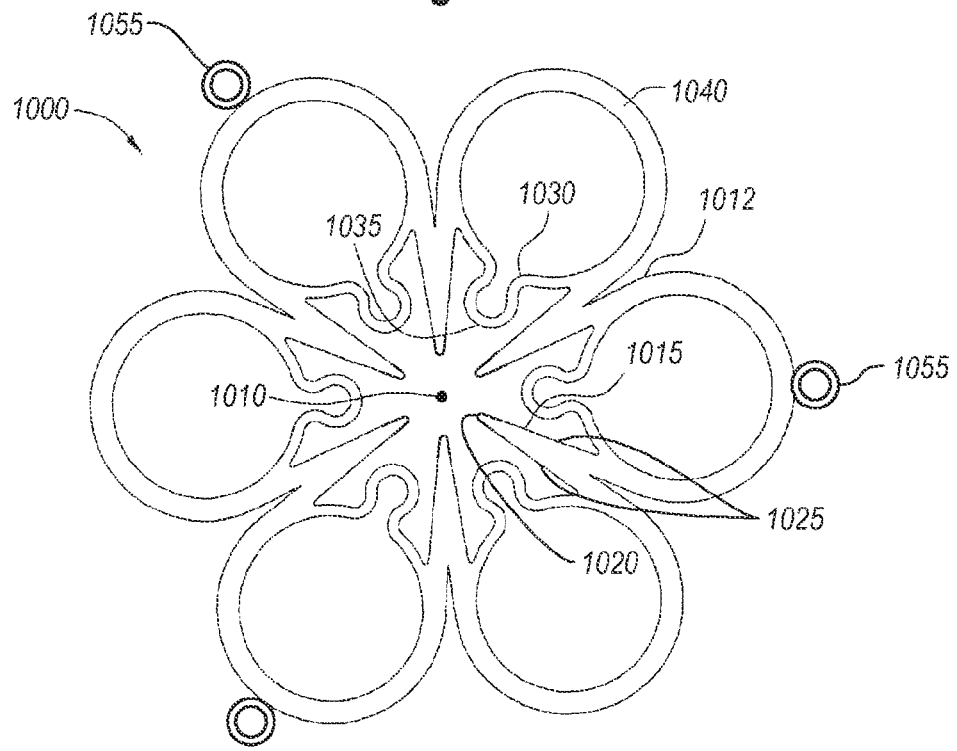
FIG. 10 illustrates another example of a closure device according to one example.

FIG. 10 illustrates, a further example of a closure device 1000. The device 1910 (not labeled) may be substantially similar to the device 900 shown in FIG. 9, with the exception of the shape of the expandable elements 1030. In the present example, rather than diamond shaped elements 930 in FIG. 9, the expandable elements 1030 may be looped elements generally defining a circular shape.

Figure 11:
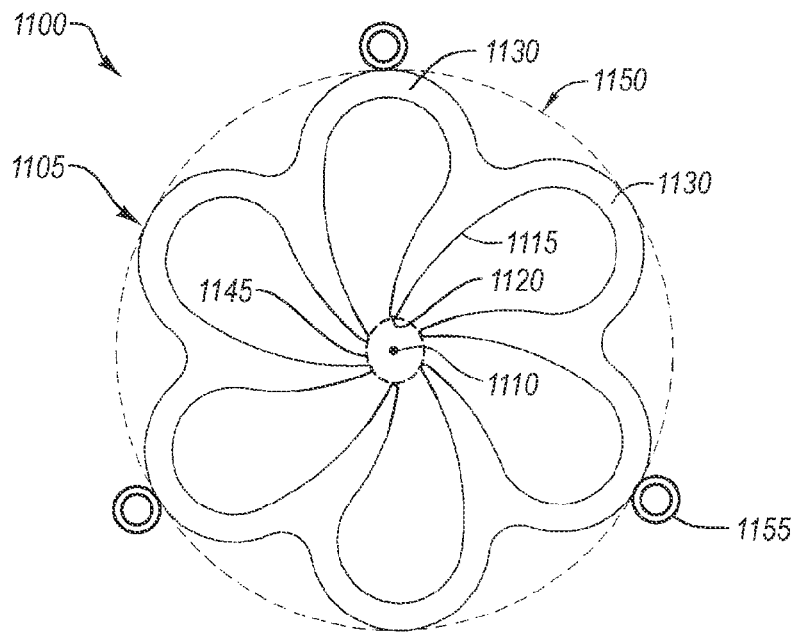
FIG. 11 illustrates a further example of a closure device according to one example.

Turning now to FIG. 11, this is another example of a closure device 1100 having device-capture features 1155. The closure device 1100 may include a body 1105 that may be generally annular-shaped and/or may define a plane. In the present example, the body 1105 may be disposed about a central axis 1110 that may extend through the plane. The body 1105 may include a plurality of outer curved elements 1130 that may extend between adjacent tissue-engaging portions 1115 and may be connected to each other to form the body 1105. When the closure device 1100 is in the deployed configuration, a substantially planar configuration in the present example as shown in FIG. 11, the curved elements 1130 may define an outer periphery 1150 of the closure device 1100.

The tissue-engaging portions 1115 may be curved or arcuately shaped and may include tip portions 1111 that may extend toward the central axis 1110 when the closure device 1100 is in a deployed configuration. The curves of the tissue-engaging portions 1115 may all be in phase with one another such that the tissue-engaging portions 1115 spiral about the central axis 1110. This may allow a length of the tissue-engaging portions 1115 to be maximized for a given diameter of the body 1105.

For example, the tissue-engaging portions 1115 may have a length that is greater than a radius of the body 1105 without the tip portions 1111 of the tissue-engaging portions 1115 touching one another. Thus, due to the arcuate shape of each tissue-engaging portion 1115, the tissue-engaging portions 1115 of the closure device 1100 may be generally longer than the straight tissue-engaging portions of the previous devices having comparable diameters. The tissue-engaging portions 1115 may, therefore, penetrate deeper into and/or apply more pressure to tissue than the tissue-engaging portions of the other devices.

The body 1105 and/or the tissue-engaging portions 1115 of the closure device 1100 may be deflected until the tissue-engaging portions 1115 extend transversely with respect to the deployed configuration, thereby defining a pre-deployed configuration (not shown), which may be transverse in the present examples. In the pre-deployed configuration, the tissue-engaging portions 1115 may be oriented substantially parallel to the central axis 1110. Additionally, the tissue-engaging portions 1115 and/or body 1105 may be biased to move from the pre-deployed configuration towards the deployed configuration. The closure device 1100 may be delivered in substantially the same manner as will be described with respect to other devices of the present invention. Similarly, the closure device 1100 may be withdrawn from engagement with the tissue by applying force to one or more of the device-capture features 1155.

Figure 12:
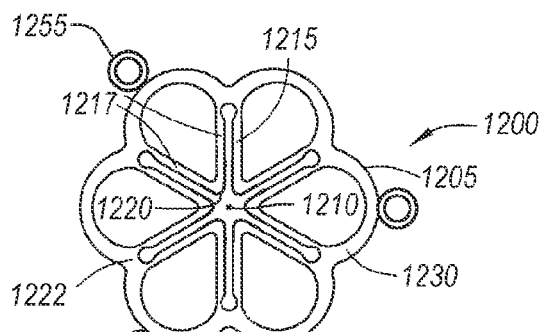
FIG. 12 illustrates a still further example of a closure device according to one example.

Turning to FIG. 12, this is another example of a device 1200 having device-capture features 1255. The device 1200 may include a peripheral body 1205 and a plurality of tissue-engaging portions 1215. Each tissue-engaging portion 1215 may include a pair of legs 1217 terminating in a tissue-engaging portion 1215. The tissue-engaging portions 1215 may be disposed substantially symmetrically about a central axis 1210. The body 1205 may include a plurality of expandable elements 1230. The expandable elements 1230 may be connected by hinged regions 1222 that may also connect adjacent tissue-engaging portions 1215.

The tissue-engaging portions 1215 may be deflected from a deployed configuration, shown in FIG. 12, to a pre-deployed configuration (not shown). In the present example, the tissue-engaging portions 1215 may be deflected such that they extend substantially transversely from the body 1205 to the pre-deployed configuration. In this pre-deployed configuration, the tissue-engaging portions 1215 may be oriented substantially parallel to the axis 1210 such that the body 1205 has a generally annular shape (not shown). The tissue-engaging portions 1215 may be biased from the pre-configured configuration towards the deployed configuration shown in FIG. 12.

The expandable elements 1230 may have a generally arcuate shape that may be expandable from a first width to a second wider width by applying a force to the device-capture features 1255, behaving similarly to the diamond-shaped cells of the example shown in FIGS. 8A-8E. Thus, the expandable elements 1230 may be biased to the expanded state, but may be compressed to the compressed state, as described above.

Figure 13:
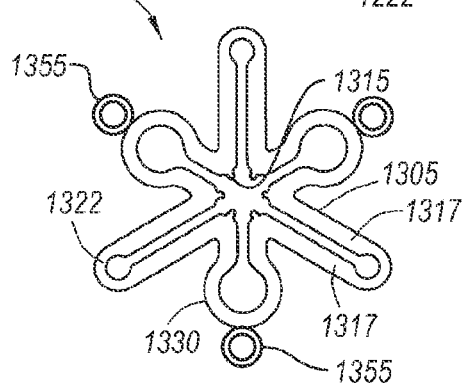
FIG. 13 illustrates an example of a closure device through tissue.

Turning to FIG. 13, this is another example of a closure device 1300 having device-capture features 1355. The device-capture features 1355 are configured to have a force applied thereto to withdraw tissue-engaging portions 1315 from engaging with the tissue. The closure device 1300 may include a peripheral body 1305 including a plurality of legs 1317 extending between tissue-engaging portions 1315, expandable elements 1330, and/or hinged regions 1322. The closure device 1300 may be formed from a single sheet of material, similar to examples described above.

The tissue-engaging portions 1315 may be biased to a deployed configuration, as shown. The body 1305 may be deflectable to a pre-deployed configuration (not shown). In the present example, the tissue-engaging portions 1305 may be oriented substantially transversely with respect to the plane of the sheet in the pre-deployed configuration. The body 1305, and particularly the legs 1317 in the present example, may be sufficiently flexible such that the closure device 1300 may assume a generally annular shape in the pre-deployed configuration, e.g., to facilitate loading of the closure device 1300 for managing access through tissue onto a delivery device (not shown).

The expandable elements 1330 may be substantially enclosed loops that may at least partially open from a compressed state (shown in FIG. 23), to an expanded state (not shown). The loops may be biased to the expanded state, similar to examples described above, thereby allowing the closure device 1300 for managing access through tissue to assume a reduced diameter and an expanded diameter.

Figure 14:
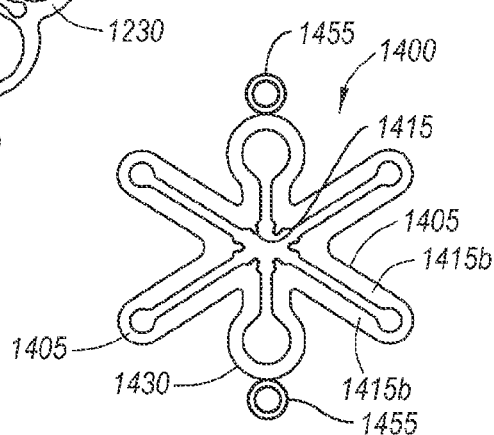
FIG. 14 illustrates another example of a closure device according to one example.

Turning to FIG. 14, this is a further example of a closure device 1400 having device-capture features 1455. The closure device 1400, in the present example, may include two expandable elements 1430. The expandable elements 1430 may be disposed in a substantially symmetrical arrangement to facilitate expansion of the closure device 1400 in a generally uniform manner.

Figure 15:
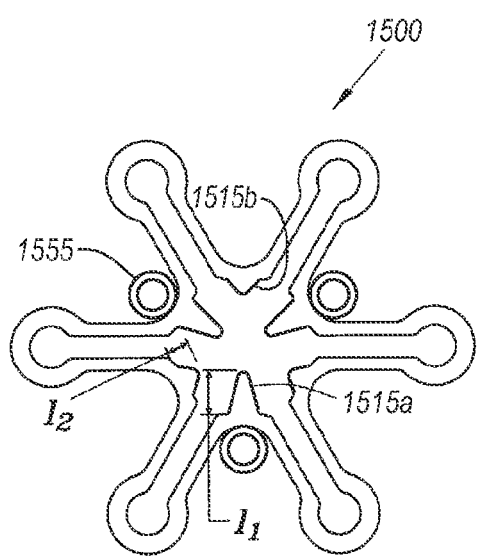
FIG. 15 illustrates a further example of a closure device according to one example.

In a further example of a closure device 1500 with device-capture features 1555 shown in FIG. 15, the closure device 1500 may include primary tissue-engaging portions 1515a having a first length $l_1$, and secondary tissue-engaging portions 1515a having a second length $l_2$ that may be substantially shorter than the first length $l_1$. In the present example, the closure device 1500 may be deployed such that the primary tissue-engaging portions 1515a penetrate into and/or engage tissue, i.e., the wall of a blood vessel, body lumen, and/or other tissue, while the secondary tissue-engaging portions 1515b may engage extra-vascular tissue, i.e., tissue between the vessel wall and the patient's skin. Thus, the closure device 1500 may simultaneously close both the opening in the vessel wall and the passage through the intervening tissue.

Figure 16:
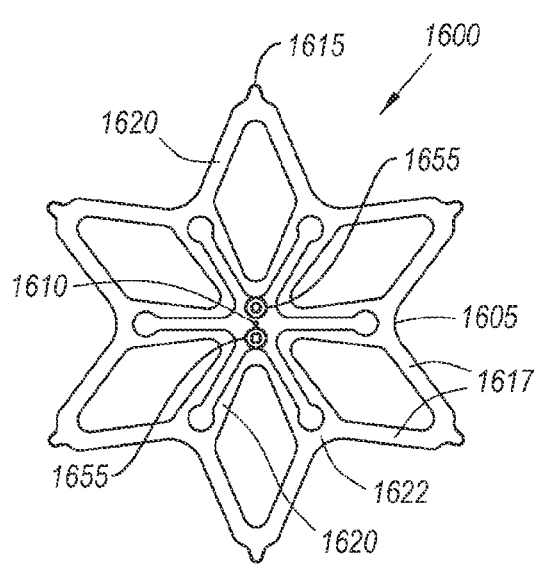
FIG. 16 illustrates a still further example of a closure device according to one example.

Turning to FIG. 16, another example of a closure device 1600 for managing access through tissue is shown, in accordance with the present invention. The closure device 1600 may include a peripheral body 1605 and a plurality of tissue-engaging portions 1615 (not labeled). Each tissue-engaging portion 1615 may include a pair of legs 1617 terminating in a tip portion 1620 configured for penetrating and/or otherwise engaging tissue. The tissue-engaging portions 1615, in the present example, may be disposed substantially symmetrically about a central axis 1610. The body 1605 may include a plurality of expandable elements 1620 that are connected by hinged regions 1622 that also connect adjacent tissue-engaging portions 1615. The expandable elements 1620 may behave similar to examples described above.

The closure device 1600 that includes device-capture features 1655. In the present example, the tissue-engaging portions 1615 may be disposed radially outward in a substantially planar configuration in the deployed configuration. The tissue-engaging portions 1615 may be deflected such that they extend from the body 1605 in a pre-deployed configuration. In the present example, the tissue-engaging portions 1615 may be deflected such that they extend from the body 1605 substantially transversely with respect to the plane defined by the sheet (similar to FIG. 8C), in a pre-deployed configuration (not shown).

The tissue-engaging portions 1615 may be biased from the pre-deployed configuration away from one another, i.e., towards the deployed configuration. Thus, with the tissue-engaging portions 1615 in the pre-deployed configuration, the tip portions 1620 may penetrate into and/or be engaged with tissue. When the closure device 1600 for managing access through tissue is released, e.g., from within a delivery device (not shown), the tissue-engaging portions 1615 may be biased to return to the deployed configuration, thereby securing the tissue with respect to the closure device.

In addition, the closure device 1600 for managing access through tissue may include expandable elements 1620 that may be expandable from a compressed state to an expanded state (similar to FIG. 8C), similar to some of the previous examples. The expandable elements 1620 may be biased to the expanded state, but may be compressed to the compressed state, e.g., by constraining the closure device 1600. Alternatively, any of the devices described herein may be biased to the compressed state but may be expanded to the expanded state, e.g., by constraining the closure device through tissue over a sheath or other elongated member.

Figure 17:
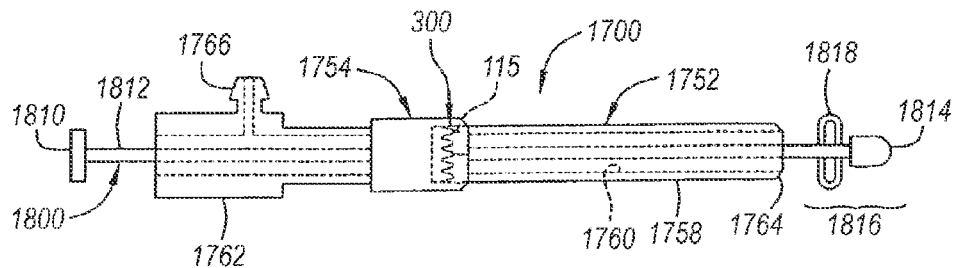
FIG. 17 illustrates an example of an apparatus suitable for delivering a closure device through tissue according to the present invention.

The devices for managing access through tissue of the present invention may be delivered using various apparatus and methods. An exemplary apparatus 1700 suitable for delivering a device 300 of the present invention is shown in FIG. 17. Other suitable apparatus that may be used to deliver a device 300 of the present invention are disclosed in co-pending U.S. patent application Ser. No. 11/427,297, entitled "Clip Applier and Methods of Use", filed Jun. 28, 2006, which is incorporated herein by reference in its entirety and which is assigned to the assignee of the present application. The disclosures of this application and any references cited therein are expressly incorporated by reference.

The apparatus 1700 may include an introducer sheath 1752 and/or a housing or carrier assembly 1754 slidably disposed on the sheath 1752. The sheath 1752 may include a substantially flexible or semi-rigid tubular body 1758 including a lumen 1760 extending between its proximal and distal ends 1762, 1764. In some embodiments, the distal end 1764 may have a size and/or shape configured to facilitate insertion into a blood vessel, e.g., having a tapered tip for facilitating substantially atraumatic introduction through the passage and at least partially into the vessel. In other embodiments, the distal end 1764 may have other sizes and/or shapes. The lumen 1760 may have a size and/or shape for inserting one or more devices therethrough. In the present embodiment, the lumen 1760 may be configured to receive one or more medical devices, such as a catheter, guide wire, and/or other medical devices (not shown). The sheath 1752 may include one or more seals (not shown), such as a hemostatic valve, within the lumen 1760 at or near the proximal end 1762 that may provide a fluid-tight seal, while yet accommodating the insertion of one or more devices into the lumen 1760 without fluid passing proximally from the sheath 1752.

Optionally, the sheath 1752 may include a side port 1766 that may communicate with the lumen 1760, for example, to deliver fluids into the lumen 1760. Alternatively, or in addition, the side port 1766 may be used to provide a "bleed back" indicator.

The apparatus 1700 may also include a mechanical locator or obturator 1800. This mechanical locator or obturator may be part of an actuator assembly (not shown) that may be attachable to the proximal end of the sheath 1752. Alternatively, the mechanical locator or obturator 1800 may be a separate device that is insertable into the lumen 1760, e.g., through the actuator assembly. Generally, the obturator 1800 may be an elongate member including a plunger handle 1810, a plunger 1812, a distal tip 1814 and a distal portion 1816. The distal tip 1814 may be substantially soft and/or flexible such that the distal tip 1814 may substantially atraumatically enter tissue. The distal portion 1816 generally includes one or more wings or other expandable elements 1818 for providing tactile feedback, as described further below.

The carrier assembly 1754 may be slidably disposed on an exterior of the sheath 1752. The carrier assembly 1754 may be configured for releasably carrying a device 300 for managing access through tissue (shown in phantom), which may incorporate elements of the various embodiments of the devices described herein. The carrier assembly 1754 may be substantially permanently attached to the sheath 1752 and/or may be actuated from the proximal end 1762 of the sheath 1752, for example, by the actuator assembly (not shown), to advance the device 300 distally during deployment. Alternatively, the device 300 may be carried by an actuator assembly.

Turning to FIGS. 18A-18F, the apparatus 1700 may be used to deliver the device 300 for managing access through tissue. In the present example, the device 300 may be used to substantially close and/or seal an incision, puncture, or other passage 1792 that extends from a patient's skin 1794, through intervening tissue 1796, and into a wall 1798 of a vessel 1790 or other body lumen. Alternatively, the apparatus 1700 may be used to deliver the device 300 to engage tissue in other procedures, e.g., to connect tissue segments together or otherwise to secure tissue structures with respect to one another. For example, the apparatus 1700 and device 300 may be used to attach an anastomosis during a bypass procedure. In another example, the apparatus 1700 and device 300 may be used to close an aperture (i.e. a puncture, cut, tear, and/or other aperture) on the surface of the patient's skin 1794. Although the device 300 and/or apparatus 1700 may be useful in a variety of procedures, the following example illustrates the usefulness of the device 300 and/or apparatus 1700 to substantially close and/or seal an incision, puncture, or other passage 1792 that extends from a patient's skin 1794, through intervening tissue 1796, and into a wall 1798 of a vessel 1790 or other body lumen.

Figure 18A:
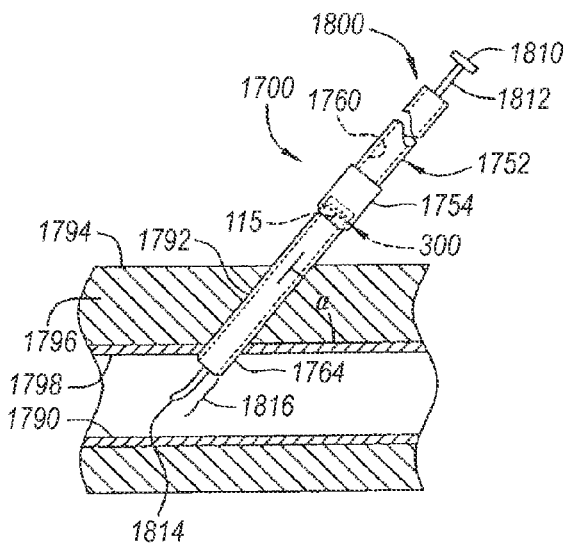
FIGS. 18A-18D are cross-sectional views of a blood vessel, showing a method for delivering a closure device through tissue into a passage communicating with the vessel using the apparatus of FIG. 17.

As shown in FIG. 18A, the sheath 1752 may be inserted or otherwise positioned within the vessel 1790, i.e., through the passage 1792. The sheath 1752 may be advanced over a guide wire or other rail (not shown) previously positioned through the passage 1792 into the vessel 1790 or advanced in conjunction with a pointed stylet directly through tissue using conventional procedures. The vessel 1790, in the present example, may be a peripheral vessel, such as a femoral, radial, or carotid artery, although other body lumens may be accessed using the sheath 1752.

The passage 1792, and consequently the sheath 1752, may be oriented at an angle "alpha" with respect to the vessel 1790, thereby facilitating introducing devices through the lumen 1760 of the sheath 1752 into the vessel 1790 with minimal risk of damage to the vessel 1790. One or more devices, such as a guide wire, a catheter, and the like (not shown), may be inserted through the sheath 1752 and advanced to a desired location within the patient's body. In the present example, the devices may be used to perform a first therapeutic or diagnostic procedure, such as angioplasty, atherectomy, stent implantation, and/or other procedure, within the patient's vasculature. In other examples, other procedures may be performed.

After the first procedure is complete, any devices used during the procedure may be removed from the sheath 1752, and the obturator 1800 may be inserted into the lumen 1760. For example, the obturator 1800 may be part of an actuator assembly (not shown), and may be advanced through the lumen when the actuator assembly is attached to the proximal end of the sheath 1752. Alternatively, the actuator assembly and obturator 1800 may be coupled separately to the sheath 1752.

When the obturator 1800 is fully inserted within the sheath 1752, the distal portion 1816 of the obturator 1800 may extend beyond the distal end 1764 of the sheath 1752. In an alternative embodiment, the obturator 1800 may be attached to an exterior surface (not shown) of the sheath 1752, for example, along a track, e.g., including cooperating slots, grooves, and the like (not shown) in the sheath 1752 and obturator 1800.

Figure 18B:
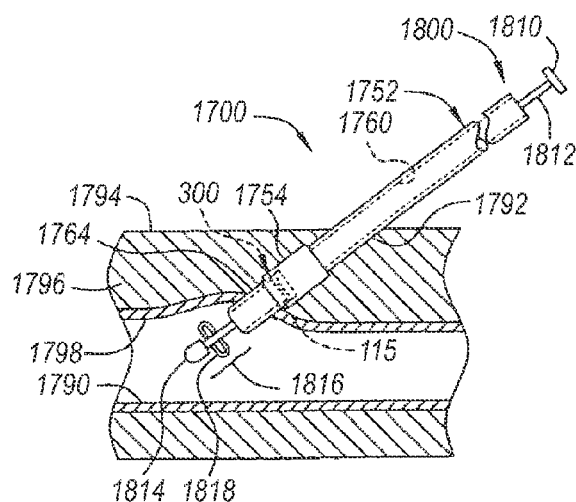

Turning to FIG. 18B, the expandable elements 1818 on the distal portion of the obturator 1800 may then be directed to their expanded configuration, for example, by activating a switch on the proximal end (not shown) of the obturator 1800. In some embodiments, the sheath 1752 and obturator 1800 may be coupled to one another, such that the sheath 1752 and obturator 1800 may be moved in conjunction with one another.

Figure 18C:
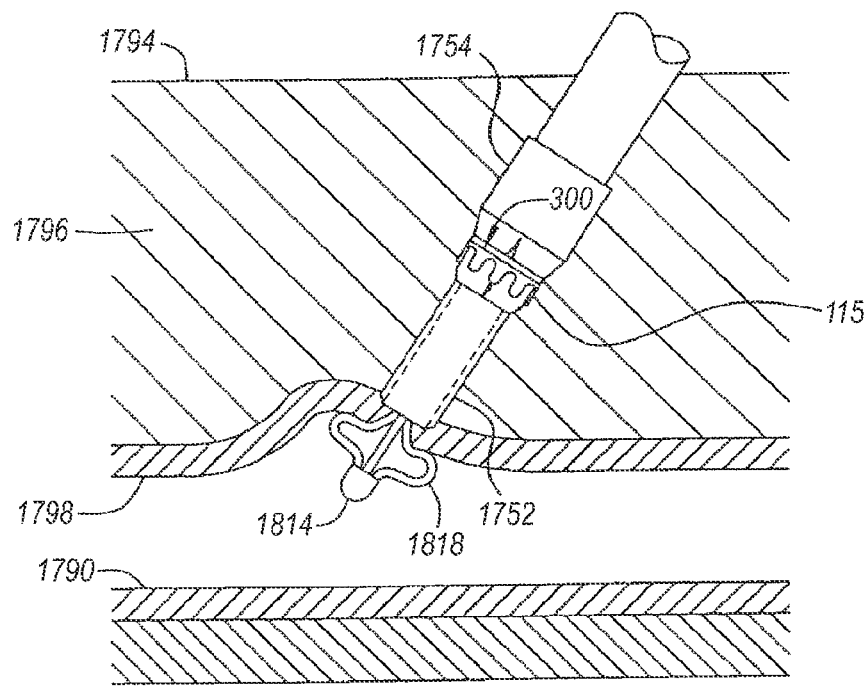

As shown in FIG. 18C, the sheath 1752 may be partially withdrawn from the vessel 1790, until the expandable elements 1818 contact the wall 1798 of the vessel 1790. Thus, the expandable elements 1818 may provide a tactile indication of the position of the sheath 1752 with respect to the wall 1798 of the vessel 1790. In addition, the expandable elements 1818 may assist in "presenting" the wall 1798 of the vessel 1790, e.g., for receiving the device 300.

Generally, the device 300 may be carried by the carrier assembly 1754 before the first procedure. The device 300 may be constrained in its pre-deployed configuration on the carrier assembly 1754, and the carrier assembly 1754 may be provided on and/or adjacent to the proximal end of the sheath 1752. Because the tissue engaging portions, which may include primary and secondary tissue engaging portions 315a, 315b may be biased towards one another, the tissue engaging portions 315a, 315b may slidably contact an inner surface (not shown) of the carrier assembly 1754 or an outer surface of the sheath 1752, thereby constraining the device 300 in its pre-deployed configuration.

Figure 18D:
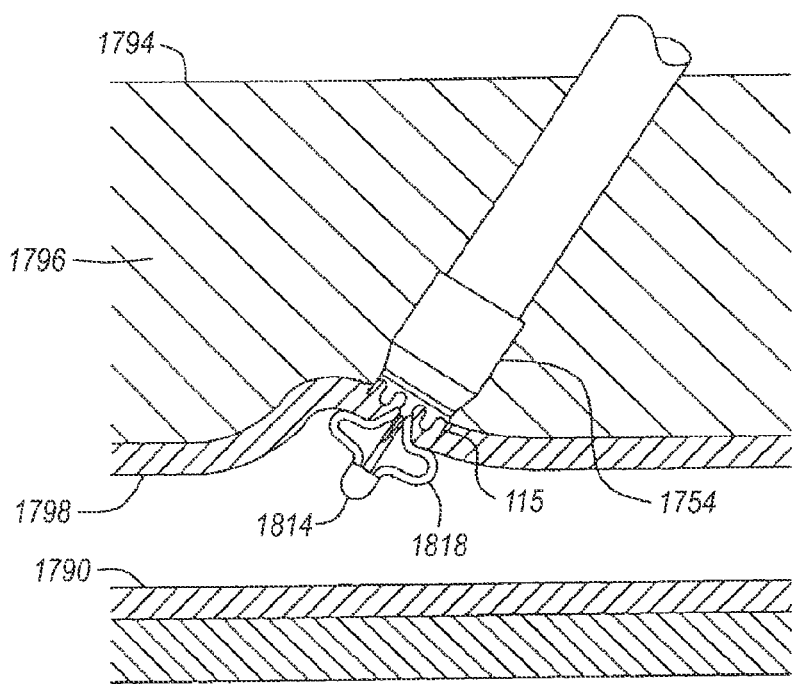

Turning to FIG. 18D, with the sheath 1752 properly positioned, the carrier assembly 1754 may then be actuated, for example, to advance the carrier assembly 1754 distally over the sheath 1752 to deliver the device 300. The carrier assembly 1754 may only be advanced a predetermined fixed distance relative to the distal end of the sheath 1752, and consequently, the expandable elements 1818 of the obturator 1800, such that the device 300 may substantially engage the wall 1798 of the blood vessel 1790. This predetermined distance may facilitate properly deploying the device 300 with respect to the wall 1798 of the vessel 1790, e.g., to prevent advancing the device 300 too far, i.e., into the vessel 1790.

As the device 300 is deployed from the carrier assembly 1754, the device 300 may be expanded to an enlarged diameter, as described, for example, in connection with FIGS. 1A-1D. In the present embodiment, a distal end of the carrier assembly 1754 may include a ramped region (not shown) that may deflect the tissue engaging portions 315a, 315b, and/or the body of the device 300 radially outwardly. As the device 300 is advanced over the ramped region, the tissue engaging portions 315a, 315b may be deflected radially outwardly, as they are being driven into the surrounding tissue, thereby engaging a larger region of tissue than if the tissue engaging portions 315a, 315b had been maintained substantially axially.

Alternatively, the device 300 may include expandable looped elements and/or spring elements (not shown), such as those described above, that may facilitate expanding the device 300 as it is deployed from the carrier assembly 1754 and/or the sheath 1752. For example, the looped elements of the device 300 may be compressed when the device 300 is loaded into the carrier assembly 1754, e.g., thereby allowing a relatively smaller profile carrier assembly 1754 to be used. The device 300 may automatically expand upon deployment from the carrier assembly 1754 to engage a larger region of tissue surrounding the opening, such as an arteriotomy 1791 in the wall 1798 of the vessel 1790 (see FIG. 19A).

Figure 19A:
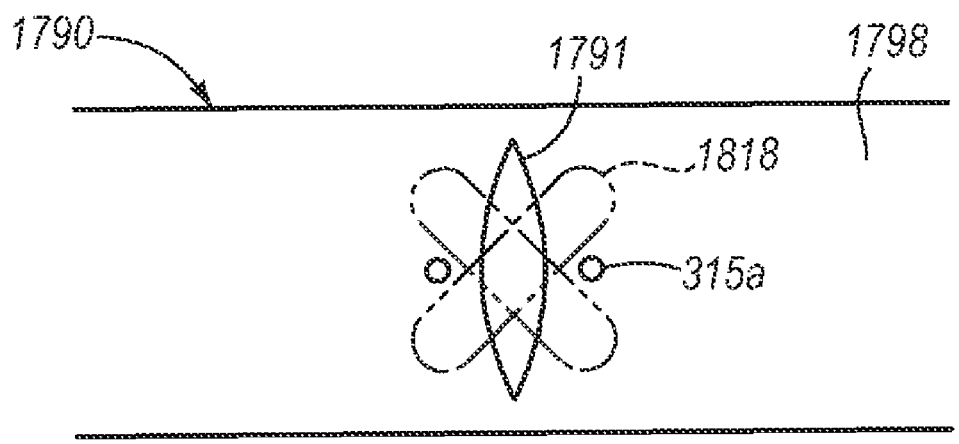
FIG. 19A is a top view of the blood vessel of FIGS. 18A-18F, showing the orientation of the expandable elements of the obturator and openings produced by primary tines of the closure device through tissue relative to an arteriotomy in the vessel.
Figure 19B:
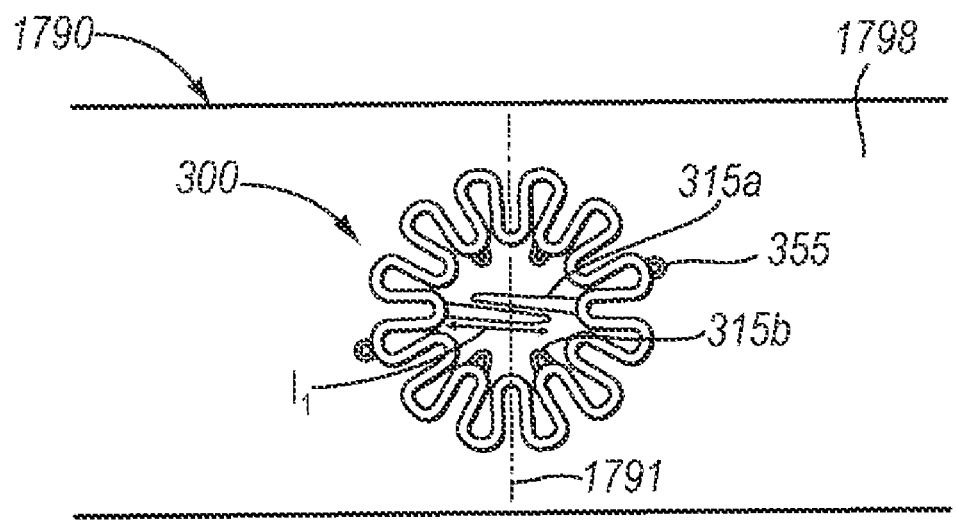
FIG. 19B is a top view of the blood vessel of FIG. 19A, showing the arteriotomy being closed by the closure device through tissue.
Figure 19C:
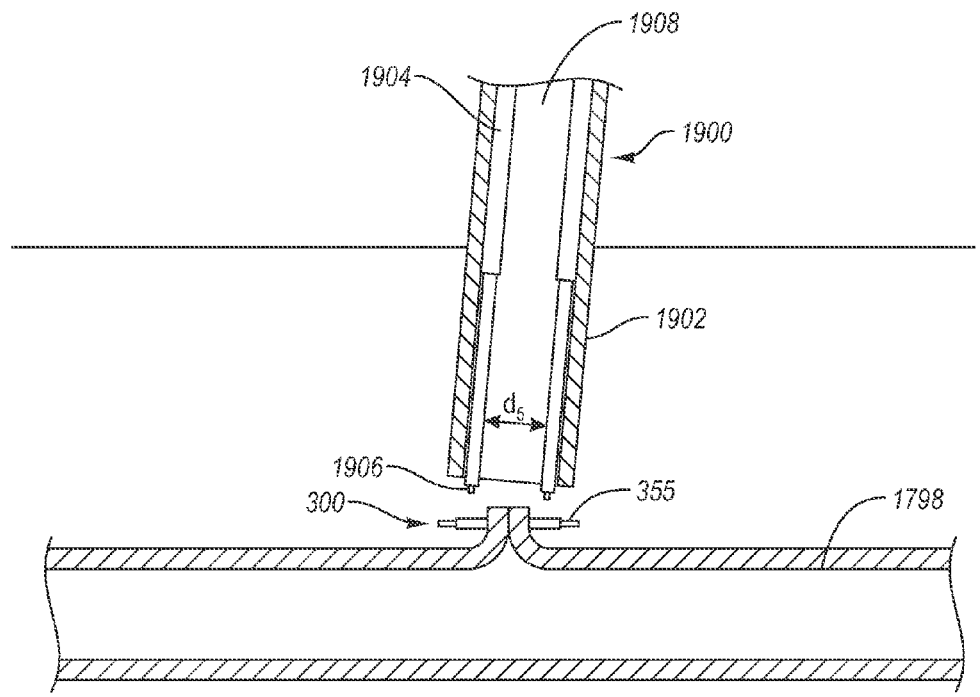
Figure 19D:
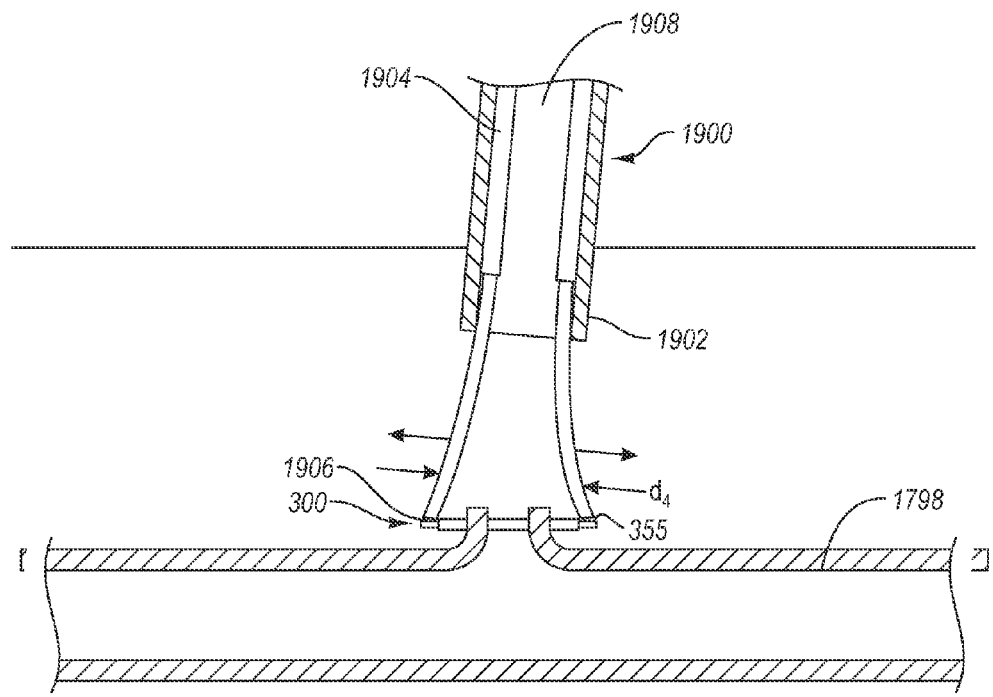
Figure 19G:
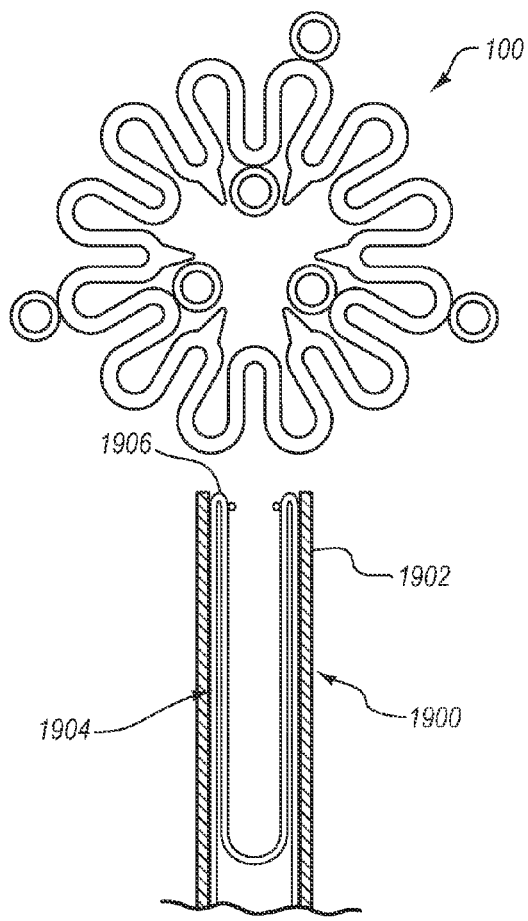
Figure 19H:
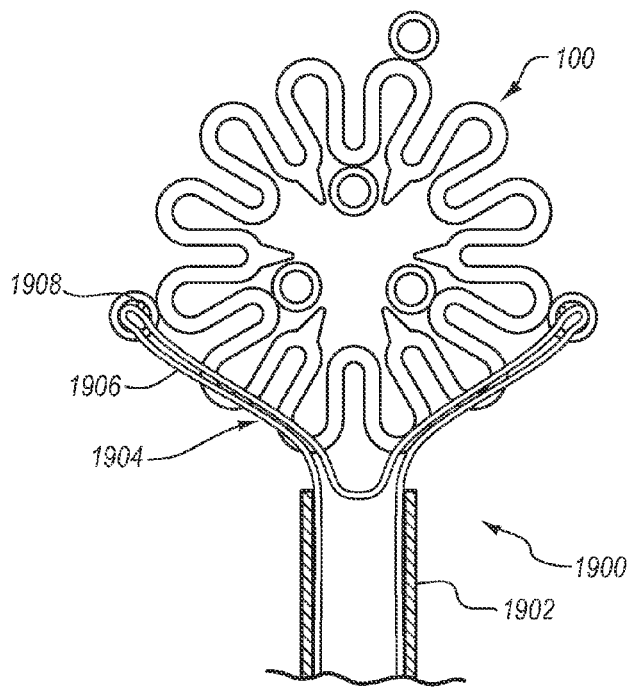

Once the device 300 is deployed entirely or otherwise released from the sheath 1752, the device 300 may resiliently move towards its deployed configuration, such as the substantially planar configuration shown in FIG. 19B. Although the length $l_1$ in FIG. 19B is illustrated as extending from a curved region (not shown), beyond the central axis, it may be possible for the length $l_1$ to be less than this distance. For instance, the length can be a length defined from a curved region to the central axis or a length defined from a curved region toward, but not passing the central axis, as discussed previously.

During delivery of the device 300, radiopaque markers (not shown) on the device 300, the carrier assembly 1754, and/or the expandable members 1818 may be monitored, e.g., using fluoroscopy, to facilitate observing and/or positioning the apparatus 1700. Thus, a relative position of the device 300 with respect to the expandable elements 1818, and consequently to the wall 1798 of the vessel 1790, may be ascertained before the device 300 is deployed from the carrier assembly 1754. Markings may also assist in locating a deployed device 300.

Turning to FIGS. 18A and 18B, in some embodiments, the expandable elements 1818 of the obturator 1800 may be rotationally offset from the one or more tissue engaging portions 315a on the device 300. For example, if the device 300 includes primary tissue engaging portions (such as those shown in FIGS. 3A-3D), the obturator 1800 and device 300 may have a predetermined relative angular orientation about the central axis 24. In the present example, the device 300 may be loaded onto the carrier assembly 1754 in a predetermined angular orientation and the obturator 1800 may be receivable in the sheath 1752 only in a predetermined angular orientation that is offset such that the tissue engaging portions 315a, 315b are out of axial alignment with the expandable elements 1818, as shown in FIG. 19A.

This predetermined rotational orientation may substantially minimize the possibility of the primary tissue engaging portions 315a contacting and/or damaging the expandable elements 1818. For example, with particular reference to FIG. 19A, a relative angular orientation of the device 300 and obturator 1800 is shown relative to an arteriotomy 1791 in the wall 1798 of the vessel 1790. Here, the expandable elements 1818 may be oriented to crisscross diagonally the arteriotomy 1791 within the interior of the vessel 1790. Because of the natural structure of the tissue in the wall of a vessel, an arteriotomy generally tends to adopt an elongate shape that extends transversely to the direction of flow (i.e., across the circumference of the vessel wall).

The primary tissue engaging portions 315a may be oriented such that the primary tissue engaging portions 315a pierce and/or engage the wall 1798 of the vessel 1790 on either side of the arteriotomy 1791, as shown. With the expandable elements 1818 crisscrossing diagonally, risk of contact with the primary tissue engaging portions 315a may be substantially reduced. Thus, in some embodiments, the primary tissue engaging portions 315a may be sufficiently long to extend entirely through the wall 1798 of the vessel 1790 while avoiding the expandable elements 1818.

The expandable elements 1818 may then be collapsed and/or withdrawn into the distal end 1764 of the sheath 1752. As the device 300 is released entirely from the sheath 1752, the primary tissue engaging portions 315a may partially overlap, as shown in FIG. 4A, thereby pulling the arteriotomy 1791 closed, similar to a single-thread suture. For example, the expandable elements 1818 may be automatically collapsed immediately before or after the device 300 is deployed from the carrier assembly 1754 or when the carrier assembly 1754 reaches its extreme distal position. In the present embodiment, the distal portion 1816 of the obturator 1800 may be collapsed and retracted into the sheath 1754 after the primary and/or secondary tissue engaging portions 315a, 315b have pierced and/or engaged the wall 1798 of the vessel 1790, but before the device 300 is entirely released from the sheath 1752.

In addition, if the device 300 includes secondary tissue engaging portions 315b (such as those shown in FIG. 19B), the secondary tissue engaging portions 315b may penetrate (partially in the present example) and/or engage the wall 1798 of the vessel 1790 during deployment of the device 300. In the present example, the lengths of the secondary tissue engaging portions 315b may be relatively short or stop members (not shown) may be provided that may prevent the primary and/or secondary tissue engaging portions 315a, 315b from piercing entirely through the wall 1798. When the device 300 is released, the primary and/or secondary tissue engaging portions 315a, 315b may pull the tissue inwardly, behaving somewhat similarly to a purse-string suture, to enhance closing the arteriotomy 1791.

Once the device 300 is successfully deployed into the wall 1798 of the vessel 1790, e.g., on either side of an arteriotomy 1791, the apparatus 1700 may be withdrawn from the passage 1792. The entire apparatus 1700 may be removed in one step, or alternatively, the obturator 1800 may first be withdrawn from the sheath 1752 before withdrawing the sheath 1752, thereby leaving the device 300 in place to close the arteriotomy 1791 and/or seal the passage 1792.

In the deployed configuration, the device 300 for managing access through tissue may substantially close and/or seal the incision, puncture, or other passage 1792 that extends from a patient's skin 1794, through intervening tissue 1796, and into a wall 1798 of a vessel 1790 or other body lumen. Alternatively, the device can be used to engage tissue in other procedures, e.g., to connect tissue segments together or otherwise to secure tissue structures with respect to one another (i.e. attach an anastomosis during a bypass procedure) and/or close an aperture (i.e. a puncture, cut, tear, and/or other aperture) on the surface of the patient's skin 1794. Following device deployment, it may be desirable to perform a second procedure and/or to remove the closure. The location of the second procedure may be through the device 300. For example, it may be desirable to provide access through the tissue and through the device 300 for performing a second therapeutic or diagnostic procedure.

As shown in FIG. 19C-19H, various expander/removal devices are illustrated. The expander/removal device 1900 may be advanced into proximity with the closure device 300. In at least one example, the expander/removal device 1900 includes a housing 1902 that houses a deployable expansion member 1904. The expansion member 1904 includes a plurality of engagement features 1906 extending from a body of the expansion member 1904. The expansion member 1904 may include any number of engagement features 1906. Further, the expansion member 1904 may include a lumen 1908 through at least a portion of the body to allow other devices or instruments to pass therethrough to access an opening in tissue, such as the arteriotomy 1791. The engagement features 1906 are configured to engage the device-capture features described herein. For ease of reference, a single type of engagement feature is discussed. It will be appreciated that any configuration of engagement features can be used to engage any combination of device-capture features.

The expander/removal device 1900 is configured to move the engagement features between at least the pre-expanded state and an expanded state. In at least one example, the engagement features 1906 are formed of a resilient material having an expanded state as a default or relaxed state in which engagement features are separated. Before deployment, at least a portion of the engagement features 1906 are located within the housing 1902.

Within the housing 1902, the location of the engagement features 1906 within the housing 1902 decreases the separation between the engagement features 1906 to a distance $d_4$ that is less than a distance $d_5$ when the engagement features 1906 engage and/or expand the device-capture features 355. In at least one example, as the engagement features 1906 are pushed distally from the housing 1902, the distance between the engagement features 1906 increases from distance $d_4$ toward a distance of $d_5$. Consequently, the distance between the engagement features 1906 may be varied by varying the location of the engagement features 1906 on the expansion member 1904.

The distance $d_5$ can be less than or approximately equal to a distance between device-capture features. The engagement features 1906 may be advanced distally of the housing 1902 to move the distance between the engagement features 1906 to approximately the same distance between device-capture features. The engagement features 1906 may then be moved into engagement with the device-capture features to thereby initiate capture with the closure device 300.

Once the engagement features 1906 have engaged the device-capture features, the distance between engagement features 1906 may be increased to expand the closure device 300. The expansion member 1904 and/or engagement features 1906 may be biased or include a "memory" to expand to the desired distance $d_5$ upon being deployed from the housing 1902. In one configuration, the expansion member 1904 and/or the engagement features 1906 can be formed of a shape memory material, such as Nitinol, to achieve this configuration. In another configuration, a separate actuator member can be disposed through the lumen 1908, engage the expansion member 1904 and/or the engagement features 1906, and move the expansion member 1904 and/or the engagement features 1906 outwardly to engage the device-capture features. This actuator member can include a shaped balloon to induce the movement, mechanically actuated expandable legs or arms, fluid actuated expandable legs or arms, combinations thereof or other structures usable to move the expansion member 1904 and/or the engagement features 1906 outwardly.

In at least one example, the device-capture features 355 may be expanded to allow access to a puncture through the closure device 300, such as to perform additional procedures. In other examples, the engagement features 355 may be expanded to disengage the closure device 300 from the wall 1798. In such examples, it may be desirable to provide axial engagement features 1908. The axis engagement features 1908 may be configured to reduce the likelihood of the engagement features 1908 from disengaging with the device-capture features as the removal/expander device 1900 draws the closure device 300 proximally.

In particular, the axial engagement features 1908 may engage the exterior portions of the device-capture features while a radial force is applied to device capture features to expand the closure device 300. In at least one example, the application of an axial force to the closure device 300 causes the closure device to twist as described above, which may maintain the contact between the exterior of the device-capture features and the engagement features 1908 to allow the closure device 300 to be fully withdrawn from the tissue. In other examples, axial engagement features 1908 and/or other configurations may be used.

Accordingly, the closure device 300 may be expanded to provide access through the tissue or the closure device 300 may be removed from the tissue. Alternatively, or more generally, the closure device 300 may be removed, moved, repositioned, or generally manipulated. The expansion of the device 300 for managing access through tissue may depend on the size of the device inserted through the device 300 for managing access through tissue, the characteristics of the device 300 (i.e. the stiffness in different directions), and/or other factors.

Embodiments of the closure device and the can expander/removal device, including the expansion members, can include a material made from any of a variety of known suitable materials, such as a shaped memory material (SMM). For example, the SMM can be shaped in a manner that allows for restriction to induce a substantially tubular, linear orientation while within a delivery shaft, but can automatically retain the memory shape of the closure device once extended from the delivery shaft. SMMs have a shape memory effect in which they can be made to remember a particular shape. Once a shape has been remembered, the SMM may be bent out of shape or deformed and then returned to its original shape by unloading from strain or heating. Typically, SMMs can be shape memory alloys (SMA) comprised of metal alloys, or shape memory plastics (SMP) comprised of polymers. The materials can also be referred to as being superelastic.

Usually, an SMA can have any non-characteristic initial shape that can then be configured into a memory shape by heating the SMA and conforming the SMA into the desired memory shape. After the SMA is cooled, the desired memory shape can be retained. This allows for the SMA to be bent, straightened, compacted, and placed into various contortions by the application of requisite forces; however, after the forces are released, the SMA can be capable of returning to the memory shape. The main types of SMAs are as follows: copper-zinc-aluminum; copper-aluminum-nickel; nickel-titanium (NiTi) alloys known as nitinol; nickel-titanium platinum; nickel-titanium palladium; and cobalt-chromium-nickel alloys or cobalt-chromium-nickel-molybdenum alloys known as elgiloy alloys. The temperatures at which the SMA changes its crystallographic structure are characteristic of the alloy, and can be tuned by varying the elemental ratios or by the conditions of manufacture.

For example, the primary material of a closure device or the expansion members can be of a NiTi alloy that forms superelastic nitinol. In the present case, nitinol materials can be trained to remember a certain shape, straightened in a shaft, catheter, or other tube, and then released from the catheter or tube to return to its trained shape. Also, additional materials can be added to the nitinol depending on the desired characteristic. The alloy may be utilized having linear elastic properties or non-linear elastic properties.

An SMP is a shape-shifting plastic that can be fashioned into a closure device or expander/removal device, including the expansion members, in accordance with the present invention. Also, it can be beneficial to include at least one layer of an SMA and at least one layer of an SMP to form a multilayered body; however, any appropriate combination of materials can be used to form a multilayered endoprosthesis. When an SMP encounters a temperature above the lowest melting point of the individual polymers, the blend makes a transition to a rubbery state. The elastic modulus can change more than two orders of magnitude across the transition temperature (Ttr). As such, an SMP can formed into a desired shape of a closure device or expander/removal device, including the expansion members, by heating it above the Ttr, fixing the SMP into the new shape, and cooling the material below Ttr. The SMP can then be arranged into a temporary shape by force, and then resume the memory shape once the force has been applied. Examples of SMPs include, but are not limited to, biodegradable polymers, such as oligo($\epsilon$-caprolactone) diol, oligo($\rho$-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present invention.

A device or member having at least one layer made of an SMM or suitable superelastic material and other suitable layers can be compressed or restrained in its delivery configuration within a delivery device using a sheath or similar restraint, and then deployed to its desired configuration at a deployment site by removal of the restraint. A device or member made of a thermally-sensitive material can be deployed by exposure of the closure device to a sufficient temperature to facilitate expansion.

Also, the device or member can be comprised of a variety of known suitable deformable materials, including stainless steel, silver, platinum, tantalum, palladium, nickel, titanium, nitinol, nitinol having tertiary materials, niobium-tantalum alloy optionally doped with a tertiary material cobalt-chromium alloys, or other known biocompatible materials. Such biocompatible materials can include a suitable biocompatible polymer in addition to or in place of a suitable metal. A device or member can include biodegradable or bioabsorbable materials, which can be either plastically deformable or capable of being set in the deployed configuration. If plastically deformable, the material can be selected to allow the device or member to be expanded in a similar manner using an expandable member so as to have sufficient radial strength and also to reduce recoil once expanded. If the polymer is to be set in the deployed configuration, the expandable member can be provided with a heat source or infusion ports to provide the required catalyst to set or cure the polymer.

In one embodiment, the closure device or other medical device, including the expander/removal device and/or the expansion members, is made from a superelastic alloy such as nickel-titanium or nitinol, and includes a ternary element selected from the group of chemical elements consisting of iridium, platinum, gold, rhenium, tungsten, palladium, rhodium, tantalum, silver, ruthenium, or hafnium. The added ternary element improves the radiopacity of the nitinol closure device or other medical device, including the expander/removal device and/or the expansion members, comparable to that of a stainless steel device or member of the same size and shape coated with a thin layer of gold. The nitinol device or member may have improved radiopacity yet may retain its superelastic and shape memory behavior and further maintains a thin strut/wall thickness for high flexibility. For example, an embodiment of a device or member may have 42.8 atomic percent nickel, 49.7 atomic percent titanium, and 7.5 atomic percent platinum.

In one embodiment, the closure device or other medical device, including the expander/removal device and/or the expansion members, can be made at least in part of a high strength, low modulus metal alloy comprising Niobium, Tantalum, and at least one element selected from the group consisting of Zirconium, Tungsten, and Molybdenum. The medical devices or members according to the present invention may provide superior characteristics with regard to bio-compatibility, radio-opacity and MRI compatibility.

Furthermore, the closure device body or other medical device, including the expander/removal device and/or the expansion members, can be formed from a ceramic material. In one aspect, the ceramic can be a biocompatible ceramic that optionally can be porous. Examples of suitable ceramic materials include hydroxylapatite, mullite, crystalline oxides, non-crystalline oxides, carbides, nitrides, suicides, borides, phosphides, sulfides, tellurides, selenides, aluminum oxide, silicon oxide, titanium oxide, zirconium oxide, alumina-zirconia, silicon carbide, titanium carbide, titanium boride, aluminum nitride, silicon nitride, ferrites, iron sulfide, and the like. Optionally, the ceramic can be provided as sinterable particles that are sintered into the shape of a closure device or layer thereof.

Moreover, the closure device body or other medical device, including the expander/removal device and/or the expansion members, can include a radiopaque material to increase visibility during placement. Optionally, the radiopaque material can be a layer or coating any portion of the device or member. The radiopaque materials can be platinum, tungsten, silver, stainless steel, gold, tantalum, bismuth, barium sulfate, or a similar material.

It is further contemplated that the external surface and/or internal surface of the devices or members (e.g., exterior and luminal surfaces) as well as the entire body can be coated with another material having a composition different from the primary material. The use of a different material to coat the surfaces can be beneficial for imparting additional properties to the device or member, such as providing radiopaque characteristics, drug-reservoirs, and improved biocompatibility.

In one embodiment, at least one biocompatible polymeric layer can be a coating that is applied over the entire device or member, or to select portions. Examples of such biocompatible polymeric materials can include a suitable hydrogel, hydrophilic polymer, hydrophobic polymer biodegradable polymers, bioabsorbable polymers, and monomers thereof. Examples of such polymers can include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), poly-hydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), combinations thereof, polymers having monomers thereof, or the like. Additionally, the coating can include hydrophilic and/or hydrophobic compounds, polypeptides, proteins, amino acids, polyethylene glycols, parylene, heparin, phosphorylcholine, or the like.

The coatings can also be provided on the device or member to facilitate the loading or delivery of beneficial agents or drugs, such as therapeutic agents, pharmaceuticals and radiation therapies. As such, the material and/or holes can be filled and/or coated with a biodegradable material.

Accordingly, the polymeric coating material can contain a drug or beneficial agent to improve the use of the endoprosthesis or other medical device, including the expander/removal device and/or the expansion members. Such drugs or beneficial agents can include antithrombotics, anticoagulants, antiplatelet agents, thrombolytics, antiproliferatives, anti-inflammatories, agents that inhibit hyperplasia, inhibitors of smooth muscle proliferation, antibiotics, growth factor inhibitors, or cell adhesion inhibitors, as well as antineoplastics, antimitotics, antifibrins, antioxidants, agents that promote endothelial cell recovery, antiallergic substances, radiopaque agents, viral vectors having beneficial genes, genes, siRNA, antisense compounds, oligionucleotides, cell permeation enhancers, and combinations thereof.

In addition to various medical devices or members, the coatings on these devices or members may be used to deliver therapeutic and pharmaceutic agents including: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), everolimus, azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors. Also, it should be recognized that many active agents have multiple pharmaceutical uses other than those specifically recited.

In one configuration, at least a portion of the external surfaces of the devices or members, such as the closure device, can include a coating comprised of polytetrafluoroethylene (PTFE), expanded PTFE (ePTFE), Dacron, woven materials, cut filaments, porous membranes, harvested vessels and/or arteries, or others such materials to form a stent graft prosthesis. Similarly, a medical device, such as a valve, a flow regulator or monitor device, can be used with the closure device, such that the closure device functions as an anchor for the medical device within the body lumen.

In one configuration, different external surfaces of a device or member, such as a low stress zone less susceptible to flexing, can be coated with functional layers of an imaging compound or radiopaque material. The radiopaque material can be applied as a layer at low stress zones of the device or member. Also, the radiopaque material can be encapsulated within a biocompatible or biodegradable polymer and used as a coating. For example, the suitable radiopaque material can be palladium platinum, tungsten, silver, stainless steel, gold, tantalum, bismuth, barium sulfate, or a similar material. The radiopaque material can be applied as layers on selected surfaces of the device or member using any of a variety of well-known techniques, including cladding, bonding, adhesion, fusion, deposition or the like.

The invention is susceptible to various modifications and alternative means, and specific examples thereof have been shown by way of example in the drawings and are herein described in detail. It should be understood, however, that the invention is not to be limited to the particular devices or methods disclosed, but to the contrary; the invention is to cover all modifications, equivalents, and alternatives falling within the spirit and scope of the claims.

What is claimed is:

1. A method, comprising:
deploying a closure element from a pre-deployed configuration to a deployed configuration and into tissue adjacent a tissue opening to substantially close the opening following a first procedure, the deployed configuration defining a plane generally parallel to the tissue adjacent the tissue opening, the closure element comprising:
a body having a plurality of expandable elements, the expandable elements moving resiliently between the pre-deployed configuration where the body is disposed out of the plane and the deployed configuration where the body is disposed about a central axis extending substantially normal to the plane and lying in the plane of the body;
a plurality of tissue-engaging portions extending from the body, at least two of the tissue-engaging portions being separated by a first distance in the deployed configuration and a second distance in the pre-deployed configuration, wherein the first distance is smaller than the second distance, and wherein the tissue-engaging portions are oriented generally towards the central axis in the deployed configuration and generally parallel to the central axis in the pre-deployed configuration, and
a plurality of device capture features operatively associated with the expandable elements, the plurality of device capture features being substantially parallel to the tissue engaging portions in the pre-deployed and deployed configurations and lying in the plane with the body in the deployed configuration;
locating the deployed closure element;
engaging the device-capture features; and
moving the device-capture features generally within the plane and in a direction opposite from that of the tissue engaging portions and radially outwardly and away from each other to increase a diameter of the body to withdraw the tissue-engaging portions from engagement with the tissue adjacent the tissue opening.

2. The method as in claim 1, wherein the tissue adjacent the tissue opening is skin.

3. The method as in claim 1, wherein the expandable elements include alternating curved elements having inner and outer curved regions.

4. The method as in claim 3, wherein moving the device-capture features to withdraw the tissue-engaging portions includes applying a force to at least one of the inner curved regions.

5. The method as in claim 3, wherein moving the device-capture features to withdraw the tissue-engaging portions includes applying a force to at least one of the outer curved regions.

6. The method of claim 1, wherein the body is biased towards the deployed configuration for biasing at least one of the tissue-engaging portions towards another tissue-engaging portion and the device capture feature is configured to move at least one of the tissue-engaging portions away from another tissue-engaging portion.

7. The method of claim 1, wherein the body comprises an inner periphery and an outer periphery and wherein at least one of the device-capture features is disposed within the inner periphery.

8. The method of claim 1, wherein the body comprises an inner periphery and an outer periphery and wherein at least one of the device-capture features is disposed generally about the outer periphery.

9. The method of claim 1, wherein the body comprises an inner periphery and an outer periphery and wherein at least one of the device-capture features is disposed outside of the outer periphery.

10. The method of claim 1, wherein the closure element further comprises a radiopaque marker and wherein the method further comprises locating the deployed closure element using the radiopaque marker.

11. The method of claim 1, wherein moving the device-capture features to withdraw the tissue-engaging portions includes moving the device-capture features in a direction away from a central axis of the closure element.

12. The method of claim 1, wherein moving the device-capture features to withdraw the tissue-engaging portions includes moving the tissue-engaging portions toward a direction being generally parallel to a central axis of the closure element.

13. The method of claim 1, wherein a pair of the plurality of device capture features are laterally offset about the central axis.

14. A method, comprising:
deploying a closure element from a pre-deployed configuration to a deployed configuration and into tissue adjacent a tissue opening to substantially close the opening following a first procedure, the deployed configuration defining a plane generally parallel to the tissue adjacent the tissue opening, the closure element comprising:
- a body having a plurality of expandable elements, the body further defining a plane in the deployed configuration, the expandable elements moving resiliently between the pre-deployed configuration where the body is disposed out of the plane and the deployed configuration where the body is disposed about a central axis extending substantially normal to the plane and lying in the plane of the body;
- a plurality of tissue-engaging portions extending from the body, at least two of the tissue-engaging portions being separated by a first distance in the deployed configuration and a second distance in the pre-deployed configuration, wherein the first distance is smaller than the second distance, and wherein the tissue-engaging portions are oriented generally towards the central axis in the deployed configuration and generally parallel to the central axis in the pre-deployed configuration, and
- a plurality of device capture features operatively associated with the expandable elements, the plurality of device capture features being laterally offset about the central axis, lying in the plane with the body, and each being disposed at an apex of an expandable element of the plurality of expandable elements;

locating the deployed closure element;
engaging the device-capture features; and
moving the device-capture generally within the plane and circumferentially outwardly and away from each other and the central axis of the body to increase a diameter of the body to withdraw the tissue-engaging portions from engagement with the tissue adjacent the tissue opening.

15. The method of claim 14, wherein the body comprises an inner periphery and an outer periphery and wherein at least one of the device-capture features is disposed within the inner periphery.

16. The method of claim 14, wherein the body comprises an inner periphery and an outer periphery and wherein at least one of the device-capture features is disposed generally about the outer periphery.

17. The method as in claim 16, wherein moving the device-capture features to withdraw the tissue-engaging portions includes applying a force to at least one of the outer curved regions.

18. The method of claim 14, wherein the body comprises an inner periphery and an outer periphery and wherein at least one of the device-capture features is disposed outside of the outer periphery.

19. The method of claim 14, wherein the closure element further comprises a radiopaque marker and wherein the method further comprises locating the deployed closure element using the radiopaque marker.

20. The method of claim 14, wherein moving the device-capture features to withdraw the tissue-engaging portions includes moving the device-capture features in a direction away from a central axis of the closure element.

21. The method of claim 14, wherein moving the device-capture features to with the tissue-engaging portions includes moving the tissue-engaging portions toward a direction being generally parallel to a central axis of the closure element.

22. A method, comprising:
deploying a closure element from a pre-deployed configuration to a deployed configuration and into tissue adjacent a tissue opening to substantially close the opening following a first procedure, the deployed configuration defining a plane generally parallel to the tissue adjacent the tissue opening, the closure element comprising:
- a body having a plurality of expandable elements that include alternating curved elements having inner and outer curved regions, the body further defining a plane in the deployed configuration, the expandable elements moving resiliently between the pre-deployed configuration where the body is disposed out of the plane and the deployed configuration where the body is disposed about a central axis extending substantially normal to the plane and lying in the plane of the body;
- a plurality of tissue-engaging portions extending from the body, at least two of the tissue-engaging portions being separated by a first distance in the deployed configuration and a second distance in the pre-deployed configuration, wherein the first distance is smaller than the second distance, where the tissue-engaging portions are oriented generally towards the central axis in the deployed configuration, and generally parallel to the central axis in the pre-deployed configuration, and
- a plurality of device capture features operatively associated with the expandable elements, the plurality of device capture features being substantially parallel to the tissue engaging portions in the pre-deployed and deployed configurations, lying in the plane with the body, and laterally offset about the central axis, wherein the body is biased towards the deployed configuration for biasing at least one of the tissue-engaging portions towards another tissue-engaging portion, and the device capture feature is configured to move at least one of the tissue-engaging portions away from another tissue-engaging portion, the closure element including a radiopaque marker;

locating the deployed closure element using the radiopaque marker;
engaging the device-capture features; and
moving the device-capture features generally within the plane and radially outwardly in a direction away from both each other and from the tissue engaging portions to increase a diameter and a circumference of the body to withdraw the tissue-engaging portions from engagement with the tissue adjacent the tissue opening.

23. The method as in claim 22, wherein moving the device-capture features to withdraw the tissue-engaging portions includes applying a force to at least one of the inner curved regions.

* * * * *